US008178567B2

(12) United States Patent
Dixson et al.

(10) Patent No.: US 8,178,567 B2
(45) Date of Patent: May 15, 2012

(54) INSECTICIDAL SUBSTITUTED AMINO HETEROCYCLIC AND HETEROARYL DERIVATIVES

(75) Inventors: John A. Dixson, Newell, SD (US); Benjamin J. Dugan, Glen Mills, PA (US); Zeinab M. Elshenawy, Holland, PA (US); Edward J. Barron, Trenton, NJ (US); Stephen F. Donovan, Revere, PA (US); Manorama M. Patel, West Windsor, NJ (US); George Theodoridis, Princeton, NJ (US); Roland Andree, Langenfeld (DE); Hans-Georg Schwarz, Langenfeld (DE); Eva-Maria Franken, Leichlingen (DE); Olga Malsam, Rösrath (DE); Christian Arnold, Langenfeld (DE)

(73) Assignee: FMC Corporation, Philadelphia, PA (US)

( * ) Notice: Subject to any disclaimer, the term of this patent is extended or adjusted under 35 U.S.C. 154(b) by 429 days.

(21) Appl. No.: 12/223,876

(22) PCT Filed: Feb. 2, 2007

(86) PCT No.: PCT/EP2007/000912
§ 371 (c)(1),
(2), (4) Date: Jan. 13, 2010

(87) PCT Pub. No.: WO2007/093292
PCT Pub. Date: Aug. 23, 2007

(65) Prior Publication Data
US 2010/0137385 A1    Jun. 3, 2010

Related U.S. Application Data

(60) Provisional application No. 60/773,755, filed on Feb. 15, 2006, provisional application No. 60/782,059, filed on Mar. 14, 2006.

(51) Int. Cl.
*A01N 43/76* (2006.01)
(52) U.S. Cl. .................................................. 514/377
(58) Field of Classification Search .................. None
See application file for complete search history.

(56) References Cited

U.S. PATENT DOCUMENTS

| | | | |
|---|---|---|---|
| 2,870,159 A | 1/1959 | Bloom | |
| 2,870,160 A | 1/1959 | Bloom | |
| 2,870,161 A | 1/1959 | Bloom | |
| 2,883,410 A | 4/1959 | Bloom | |
| 3,509,170 A | 4/1970 | Levitt | |
| 3,636,219 A | 1/1972 | Culik et al. | |
| 3,679,798 A | 7/1972 | Culik et al. | |
| 4,732,908 A | 3/1988 | Burckhardt | |

| | | | |
|---|---|---|---|
| 2009/0012070 A1 | 1/2009 | Dixson et al. | |
| 2009/0036306 A1 | 2/2009 | Dixson et al. | |
| 2009/0209422 A1 | 8/2009 | Dixson et al. | |

FOREIGN PATENT DOCUMENTS

| | | | |
|---|---|---|---|
| DE | 19 63 192 A1 | | 6/1971 |
| DE | 1963192 | * | 6/1971 |
| EP | 0 135 105 A1 | | 3/1985 |
| EP | 0 251 453 A2 | | 1/1988 |
| WO | WO 03/092374 A2 | | 11/2003 |
| WO | WO 2007/020377 A2 | | 2/2007 |
| WO | WO 2007/060121 A1 | | 5/2007 |

OTHER PUBLICATIONS

Buśko-Oszczapowicz, I. & Oszczapowicz, J., "Detection and determination of imidic acid derivatives," *Amidines and Imidates* 2:259-262, John Wiley & Sons, Ltd., Chichester, UK (1991).
Shukla, U.K., et al., "Synthesis of *trans*-2-[N-(2-Hydroxy-1,2,3,4-Tetrahydro-Naphthalene-1-YL)]Iminothiazolidine and Related Compounds—A New Class of Antidepressants," *Collect. Czech. Chem. Commun.* 57:415-424, Institute of Organic Chemistry and Biochemistry, Czech Republic (1992).
Wong, W.C., et al., "A Convenient Synthesis of 2-Amino-2-Oxazolines and their Pharmacological Evaluation at Cloned Human α Adrenergic Receptors," *Bioorganic & Medicinal Chemistry Letters* 4:2317-2322, Elsevier Science Ltd., Great Britain (1994).
English language translation of the claims of patent specification for DE 19 63 192 A1, filed Jun. 24, 1971.
International Search Report and Written Opinion of the International Searching Authority for Application No. PCT/EP2007/000912, European Patent Office, Rijswijk, The Netherlands, mailed on Oct. 29, 2007.

(Continued)

*Primary Examiner* — Rebecca Anderson
*Assistant Examiner* — Alicia L Otton
(74) *Attorney, Agent, or Firm* — FMC Corporation

(57) ABSTRACT

Certain substituted amino heterocyclic and heteroaryl derivatives have provided unexpected insecticidal and acaricidal activity. These compounds are represented by formula (I): wherein R, $R^1$, $R^2$, $R^3$, $R^4$, A, B and Q are fully described herein. In addition, compositions comprising an insecticidally effective amount of at least one compound of formula I, and optionally, an effective amount of at least one of an additional compound, with at least one insecticidally compatible carrier are also disclosed; along with methods of controlling insects comprising applying said compositions to a locus where insects are present or are expected to be present.

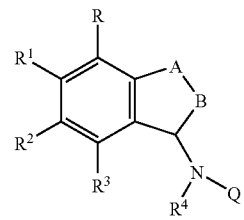

(I)

2 Claims, No Drawings

OTHER PUBLICATIONS

First Examiner's Report for Chilean Application No. 404-07, Instituto Nacional de Propiedad Industrial, Chile, mailed on Apr. 15, 2009.

Partial English translation, dated Jul. 9, 2009, of the First Examiner's Report for Chilean Application No. 404-07, Instituto Nacional de Propiedad Industrial, Chile, mailed on Apr. 15, 2009.

Second Examiner's Report for Chilean Application No. 404-07, Instituto Nacional de Propiedad Industrial, Chile, mailed on Mar. 17, 2010.

Partial explanation of the Second Examiner's Report for Chilean Application No. 404-07, dated Apr. 30, 2010, Instituto Nacional de Propiedad Industrial, Chile, mailed on Mar. 17, 2010.

* cited by examiner

INSECTICIDAL SUBSTITUTED AMINO HETEROCYCLIC AND HETEROARYL DERIVATIVES

FIELD OF THE INVENTION

The present invention generally relates to pesticidal compounds and their use in controlling insects and acarids. In particular, it pertains to compositions of pesticidal substituted amino heterocyclic and heteroaryl derivatives and agriculturally acceptable salts thereof, methods for their use in controlling insects and acarids and novel intermediates thereto.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structure. Although there are many orders of insects that can cause significant crop damage, insects, for example, of the order "Homoptera" are of major importance. The order Homoptera includes, for example, aphids, leafhoppers, cicadas, whiteflies, and mealybugs. Homoptera have piercing/sucking mouthparts, enabling them to feed by withdrawing sap from vascular plants. Insect damage from Homoptera is manifested in several different ways, other than damage caused by direct feeding. For example, many species excrete honeydew, a sticky waste product that adheres to plants upon which the insect feeds and lives. Honeydew alone causes cosmetic injury to crop plants. Sooty molds will often grow on honeydew, making food products or ornamental plants look unappealing, thereby reducing their cosmetic and economic value. Some Homoptera have toxic saliva that is injected into plants while they are feeding. The saliva can cause plant damage through disfigurement and in some instances plant death. Homoptera can also vector disease-causing pathogens. Unlike direct damage, it does not take a large number of disease-vectoring insects to cause considerable damage to crop plants.

Thus, there is a continuing demand for new insecticides, and for new acaricides that are safer, more effective, and less costly. Insecticides and acaricides are useful for controlling insects and acarids which may otherwise cause significant damage both above and below the soil level to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of articles and patents disclose some substituted amino heterocyclic and heteroaryl compounds that are reported to have pharmaceutical and veterinary uses. For example, an article in Collect. Czech. Chem. Commun. (Vol 57) (1992) pages 415-424, describes the synthesis and testing of potential antidepressant and antiparasitic agents of the following structures:

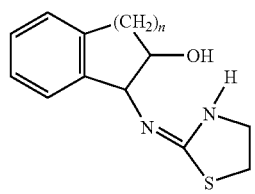

VIII, n = 2
IX, n = 1 and

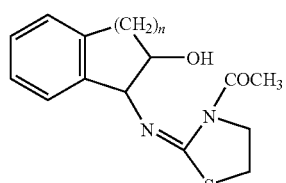

X, n = 2
XI, n = 1

Antidepressant activity was exhibited by compound VIII, none of the compounds exhibited antiparasitic activity.

U.S. Pat. No. 2,870,161 discloses and claims substituted and unsubstituted 2-(1-indanylamino)-oxazolines, useful as tranquilizing agents, of the following structure:

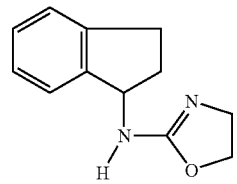

wherein;

(a) the substituents on a substituted indanyl ring are selected from the group consisting of one to three alkyl, alkoxy and thioalkyl groups each containing up to four carbon atoms, and one to three chlorine, bromine and iodine atoms and,
(b) each substituent on a substituted methylene group of the oxazoline ring is selected from the group consisting of alkyl groups each containing one to four carbon atoms, there being a total of from one to eight carbon atoms in such substituents.

U.S. Pat. No. 2,883,410 claims substituted and unsubstituted N-(1-indanyl)-N'-(β-substituted ethyl)-ureas as intermediates and as active central nervous system regulators of the following structure:

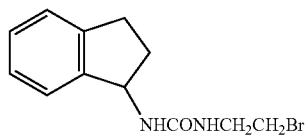

wherein the bromine may be replaced with other halogens such as chlorine or iodine, or with alkyl or aryl sulfonyl groups such as methanesulfonyloxy or p-toluenesulfonyloxy. The hydrogen atoms in the indanyl group may be replaced with one to three alkyl, alkoxy and thioalkyl groups each containing up to four carbon atoms, as well as from one to three chlorine, bromine or iodine atoms. The alpha and beta carbon atoms of the ethyl portion of the ureas can contain substituents which may be alkyl groups of one to four carbon atoms.

U.S. Pat. No. 2,870,160 discloses substituted and unsubstituted N-(3-benzofuranylamino)-oxazolines, useful as tranquilizing agents, of the following structure:

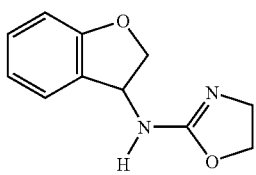

wherein;
(a) the substituents on a substituted indanyl ring are selected from the group consisting of one to three alkyl, alkoxy and thioalkyl groups each containing up to four carbon atoms, and one to three chlorine, bromine and iodine atoms and,
(b) each substituent on a substituted methylene group of the oxazoline ring is selected from the group consisting of alkyl groups each containing one to four carbon atoms, there being a total of from one to eight carbon atoms in such substituents.

Also disclosed in this U.S. patent are substituted and unsubstituted N-(3-benzofuranyl)-N'-(O-substituted ethyl)-ureas as intermediates and as active central nervous system regulators of the following structure:

wherein the bromine may be replaced with other halogens such as chlorine or iodine, or with alkyl or aryl sulfonyl groups such as methanesulfonyloxy or p-toluenesulfonyloxy. The hydrogen atoms in the indanyl group may be replaced with one to three alkyl, alkoxy and thioalkyl groups each containing up to four carbon atoms, as well as from one to three chlorine, bromine or iodine atoms. The alpha and beta carbon atoms of the ethyl portion of the ureas can contain substituents which may be alkyl groups of one to four carbon atoms.

U.S. Pat. No. 2,870,159 discloses and claims substituted and unsubstituted hydrogenated 2-(1-naphthylamino)-oxazolines, useful as tranquilizing agents, of the following structure:

wherein;
(a) the substituents on a substituted 1,2,3,4-tetrahydronaphthyl ring are selected from the group consisting of one to three alkyl, alkoxy and thioalkyl groups each containing up to four carbon atoms, and one to three chlorine, bromine and iodine atoms and, (b) each substituent on a substituted methylene group of the oxazoline ring is selected from the group consisting of alkyl groups each containing one to four carbon atoms, there being a total of from one to eight carbon atoms in such substituents.

Also disclosed in this U.S. patent are substituted and unsubstituted N-(1-reduced naphthyl)-N'-(β-substituted ethyl)-ureas as intermediates and as active central nervous system regulators of the following structure:

wherein the bromine may be replaced with other halogens such as chlorine or iodine, or with alkyl or aryl sulfonyl groups such as methanesulfonyloxy or p-toluenesulfonyloxy. The hydrogen atoms in the indanyl group may be replaced with one to three alkyl, alkoxy and thioalkyl groups each containing up to four carbon atoms, as well as from one to three chlorine, bromine or iodine atoms. The alpha and beta carbon atoms of the ethyl portion of the ureas can contain substituents which may be alkyl groups of one to four carbon atoms.

U.S. Pat. No. 3,636,219 discloses pharmaceutical compositions containing certain thiazolines and imidazolines, useful for both human and veterinary applications, in which the thiazolines and imidazolines include compounds of the following structures:

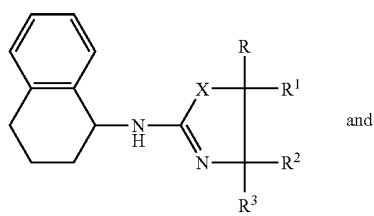

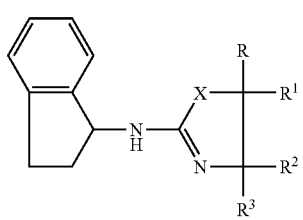

wherein;
X is S or N; R, $R^1$, $R^2$ and $R^3$ are the same or different and can be hydrogen, or an alkyl group of 1 through 4 carbon atoms with a total number of carbon atoms in these 4 substituents being a maximum of 8. In the compounds of formula (2) and (3) the hydrogen atoms in the partially reduced naphthyl or the indanyl groups may be replaced with substituents such as halogen, alkyl of 1 through 4 carbons, alkoxy of 1 through 4 carbons, alkylthio of 1 through 4 carbons, trifluoromethyl and trifluoromethoxy. Up to three such substituents can be present.

U.S. Pat. No. 3,679,798 discloses pharmaceutical compositions containing arylaminooxazoline and an antichlolineric agent, useful for both human and veterinary applications, in which the arylaminooxazoline includes compounds of the following structures:

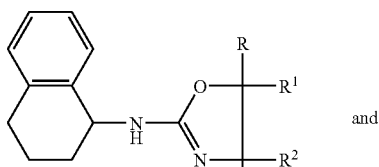
(2)

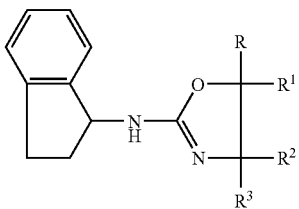
(3)

wherein;
R, R¹, R² and R³ are the same or different and can be hydrogen, or an alkyl group of 1 through 4 carbon atoms with a total number of carbon atoms in these 4 substituents being a maximum of 8. In the compounds of formula (2) and (3) the hydrogen atoms in the partially reduced naphthyl or the indanyl groups may be replaced with substituents such as halogen, alkyl of 1 through 4 carbons, alkoxy of 1 through 4 carbons, alkylthio of 1 through 4 carbons, trifluoromethyl and trifluoromethoxy. Up to three such substituents can be present.

Offenlegungsschrift 1,963,192 discloses and claims ectoparasiticidal oxazolidine compounds of the formula:

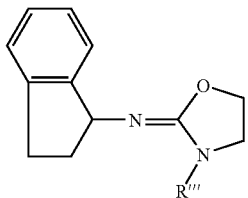

wherein
R'" is hydrogen or methyl.

U.S. Pat. No. 3,509,170 discloses heterocyclic amino-oxazolines, which exhibit pharmaceutical properties, including central nervous system depressant activity, of the following structures:

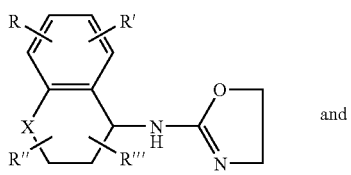
(1)

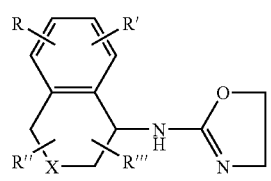
(2)

wherein;
X is oxygen, sulfur or methylamino;
R is hydrogen or alkyl of 1 through 4 carbon atoms;
R' is hydrogen, alkyl of 1 through 4 carbon atoms, alkoxy of 1 through 4 carbon atoms, alkylthio of 1 through 4 carbon atoms, dimethylamino, fluorine, chlorine or bromine;
R" is hydrogen or alkyl of 1 through 4 carbon atoms; and
R'" is hydrogen or alkyl of 1 through 4 carbon atoms as well as intermediates for the synthesis of such compounds.

There is no disclosure or suggestion in any of the above-referenced patents or publications of the insecticidal activity of the compounds of the present invention against members of the order "Homoptera". In addition, there is no disclosure or suggestion in any of the above-referenced patents or publications of the structures of the novel compounds of the present invention.

SUMMARY OF THE INVENTION

The present invention generally relates to insecticidal and acaricidal compositions of substituted amino heterocyclic and heteroaryl derivatives and to certain new and useful compounds, namely certain substituted amino heterocyclic and heteroaryl derivatives that are surprisingly active in the control of insects and acarids when used in the insecticidal and acaricidal compositions and methods of this invention. and to novel intermediates useful in preparing the compounds of the present invention. The insecticidal and acaricidal compositions of the present invention are comprised of at least one of an insecticidally effective amount of a compound of formula I and at least one insecticidally compatible carrier therefor, wherein the compound of formula I is:

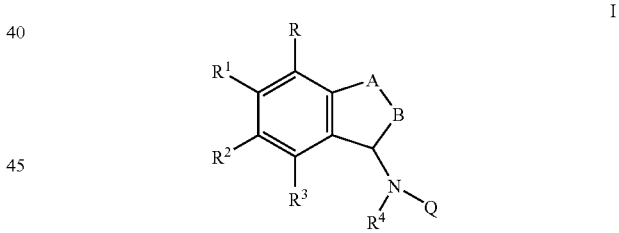
I wherein
A is —CHR⁵—, —CHR⁵CHR⁶—, —O—, —S(O)$_n$—, —NR⁷—, —OCHR⁵—, —CHR⁵O—, —S(O)$_n$CHR⁵—, —CHR⁵S(O)$_n$—, —C(X)— or —C(=NOR⁷)—;
B is —CHR⁸—, —O— or —S(O)$_n$—;
n is an integer selected from 0, 1 or 2;
R, R¹, R² and R³ are independently selected from hydrogen, halogen, hydroxy, alkyl, alkoxy, haloalkyl, haloalkoxy, haloalkylthio, alkenyl, haloalkenyl, alkynyl, haloalkynyl, cyano, nitro, aryl, aryloxy, heteroaryl, alkoxyalkyl, alkoxyalkoxyalkyl, cycloalkyl, cyanoalkyl, formal, alkoxycarbonyl, acetyl, alkylcarbonyl, alkenylcarbonyl, dialkylphosphonato, SF₅, amino, mono- and dialkylamino, cycloalkylamino, (cycloalkyl)(alkyl)amino, alkylthio, sulfonyl, alkylsulfonyl, haloalkylsulfonyl, alkylsulfinyl, alkylsulfinylalkyl, alkylsulfonylalkyl, alkylthiocarbonyl and hydroxycarbonyl;

Q is selected from:

(C) 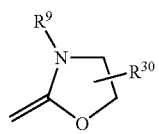

(D) 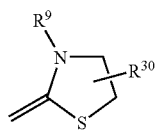

(E) 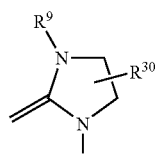

(F) 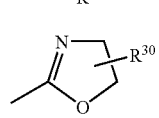

(G) 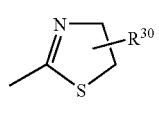

(H) 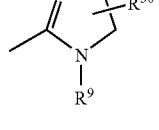

(J) 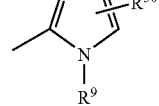

(K) 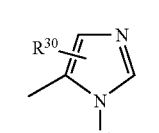

(L) 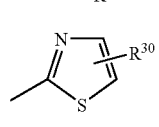

(M) 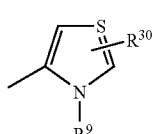

(N) 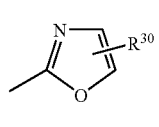

(O) 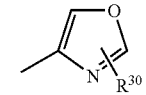

where
$R^4$ is taken together with the connecting atom in Q to form a double bond as in (C), (D) and (E) or
$R^4$ and $R^9$ are independently selected from hydrogen, cyano, nitro, arylalkyl, 2-oxazoline, 2-thiazoline, 2-imidazoline, —C(X)R$^{10}$, —C(X)OR$^{11}$, —C(X)SR$^{11}$, —S(O)$_n$R$^{11}$, —C(X)NR$^{12}$R$^{13}$, —S(O)$_n$NR$^{12}$R$^{13}$, —P(X)(OR$^{14}$)(OR$^{15}$), —P(X)(NR$^{16}$R$^{17}$)(NR$^{18}$R$^{19}$), —CHR$^{20}$—X—R$^{21}$, —CH=NR$^{22}$ and —C(=NR$^{31}$)(SR$^{32}$);
where X is oxygen or sulfur; $R^{10}$ is hydrogen or alkyl; $R^{11}$ is hydrogen, alkyl, haloalkyl, hydroxyalkyl, hydroxycarbonylalkyl, alkoxycarbonylalkyl, or —NR$^{10}$CO$_2$R$^{10}$; $R^{12}$ and $R^{13}$ are independently selected from hydrogen, alkyl, haloalkyl, cycloalkyl, cyanoalkyl, aryl, alkylcarbonyl, alkoxycarbonyl, alkoxycarbonylalkyl, alkoxyalkyl, alkylthioalkyl, alkylsulfinylalkyl, alkylsulfonylalkyl, mono or dialkylaminocarbonylalkyl, aminoalkyl, mono or dialkylaminoalkyl and arylcarbonyl; $R^{14}$ and $R^{15}$ are independently selected from hydrogen, alkyl and haloalkyl; $R^{16}$, $R^{17}$, $R^{18}$ and $R^{19}$ are independently selected from hydrogen and alkyl; $R^{20}$ is hydrogen or alkyl; $R^{21}$ is alkyl, haloalkyl, —C(X)R$^{23}$ or —P(X)(OR$^{24}$)(OR$^{25}$); $R^{22}$ is hydrogen, alkyl, haloalkyl, hydroxy, alkoxy, haloalkoxy, cyano, pyridinyl or 2-thiazolinyl; $R^{23}$ is hydrogen, alkyl or haloalkyl; $R^{24}$ and $R^{25}$ are independently selected from hydrogen, alkyl and haloalkyl; $R^{31}$ and $R^{32}$ are independently selected from hydrogen, alkyl, arylalkyl, —C(X)R$^{10}$, —CO$_2$R$^{11}$, —S(O)$_n$R$^{11}$, —C(X)NR$^{12}$R$^{13}$, —S(O)$_n$NR$^{12}$R$^{13}$, —P(X)(OR$^{14}$)(OR$^{15}$), —P(X)(NR$^{16}$R$^{17}$)(NR$^{18}$R$^{19}$) and —CHR$^{20}$—X—R$^{21}$;
$R^5$ is selected from hydrogen, halogen, hydroxy, alkyl, alkoxy, alkylthio, haloalkyl, haloalkoxy, aryl, cyano and nitro;
$R^6$ is selected from hydrogen, halogen, hydroxy, alkyl, alkoxy, alkylthio, haloalkyl, haloalkoxy, aryl, cyano and nitro;
$R^7$ is hydrogen or alkyl;
$R^8$ is hydrogen, halogen, alkyl, alkoxy or aryl;
$R^{30}$ is hydrogen, halogen or alkyl;
and
agriculturally acceptable salts thereof.

One skilled in the art will, of course, recognize that within the description set forth above, when A is selected from —, —O—, —S(O)$_n$—, —NR$^8$—, —CHR$^6$O— and —CHR$^6$S(O)$_n$— then B is not selected from —O— or —S(O)$_n$—.

When Q is (E), then both $R^9$ may be the same or different.

The present invention is also directed to certain novel substituted ethyl carboxamide and thiocarboxamide intermediates represented by formula IA:

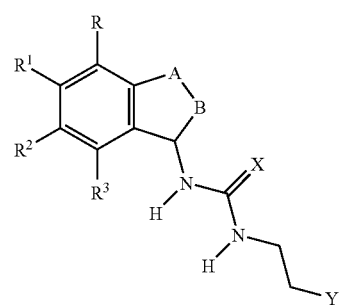

IA wherein

A is —CHR$^5$—, —CHR$^5$CHR$^6$—, —O—, —S(O)$_n$—, —NR$^7$—, —OCHR$^5$—, —CHR$^5$O—, —S(O)$_n$CHR$^5$—, —CHR$^5$S(O)$_n$—, —C(O)—, —C(S)— or —C(=NOR$^7$)—;

B is —CHR$^8$—, —O— or —S(O)$_n$—;

n is an integer selected from 0, 1 and 2;

R, R$^1$, R$^2$ and R$^3$ are independently selected from hydrogen, halogen, hydroxy, alkyl, alkoxy, haloalkyl, haloalkoxy, haloalkylthio, alkenyl, haloalkenyl, alkynyl, haloalkynyl, cyano, nitro, aryl, aryloxy, heteroaryl, alkoxyalkyl, alkoxyalkoxyalkyl, cycloalkyl, cyanoalkyl, formal, alkoxycarbonyl, acetyl, alkylcarbonyl, alkenylcarbonyl, dialkylphosphonato, SF$_5$, amino, mono- and dialkylamino, cycloalkylamino, (cycloalkyl)(alkyl)amino, alkylthio, sulfonyl, alkylsulfonyl, haloalkylsulfonyl, alkylsulfinyl, alkylsulfinylalkyl, alkylsulfonylalkyl, alkylthiocarbonyl and hydroxycarbonyl;

X is oxygen or sulfur; and

Y is chlorine, bromine, iodine, methanesulfonyloxy or p-toluenesulfonyloxy.

The present invention is also directed to compositions containing an insecticidally effective amount of at least one of a compound of formula I, and optionally, an effective amount of at least one of an additional compound, with at least one agriculturally acceptable extender or adjuvant.

The present invention is also directed to methods of controlling insects, where control is desired, which comprise applying an insecticidally effective amount of the above composition to the locus of crops, or other areas where insects are present or are expected to be present. Other aspects of the present invention will become apparent.

DETAILED DESCRIPTION OF THE INVENTION

The present invention generally relates to insecticidal and acaricidal compositions of substituted amino heterocyclic and heteroaryl derivatives and to certain new and useful compounds, namely certain substituted amino heterocyclic and heteroaryl derivatives that are surprisingly active in the control of insects and acarids when used in the insecticidal and acaricidal compositions and methods of this invention and to novel intermediates useful in preparing the compounds of the present invention. The insecticidal and acaricidal compositions of the present invention are comprised of at least one of an insecticidally effective amount of a compound of formula I and at least one insecticidally compatible carrier therefor, wherein the compound of formula I is:

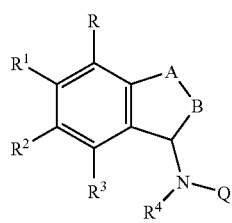

I wherein

A is —CHR$^5$—, —CHR$^5$CHR$^6$—, —O—, —S(O)$_n$—, —NR$^7$—, —OCHR$^5$—, —CHR$^5$O—, —S(O)$_n$CHR$^5$—, —CHR$^5$S(O)$_n$—, —C(O)—, —C(S)— or —C(=NOR$^7$)—;

B is —CHR$^8$—, —O— or —S(O)$_n$—;

n is an integer selected from 0, 1 or 2;

R, R$^1$, R$^2$ and R$^3$ are independently selected from hydrogen, halogen, hydroxy, alkyl, alkoxy, haloalkyl, haloalkoxy, haloalkylthio, alkenyl, haloalkenyl, alkynyl, haloalkynyl, cyano, nitro, aryl, aryloxy, heteroaryl, alkoxyalkyl, alkoxyalkoxyalkyl, cycloalkyl, cyanoalkyl, formal, alkoxycarbonyl, acetyl, alkylcarbonyl, alkenylcarbonyl, dialkylphosphonato, SF$_5$, amino, mono- and dialkylamino, cycloalkylamino, (cycloalkyl)(alkyl)amino, alkylthio, sulfonyl, alkylsulfonyl, haloalkylsulfonyl, alkylsulfinyl, alkylsulfinylalkyl, alkylsulfonylalkyl, alkylthiocarbonyl and hydroxycarbonyl;

Q is selected from:

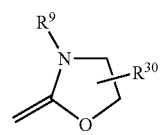

(C)

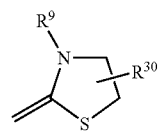

(D)

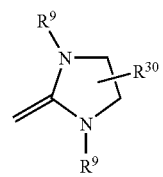

(E)

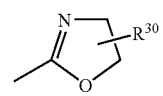

(F)

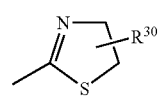

(G)

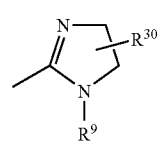

(H)

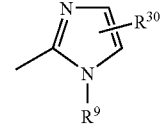

(J)

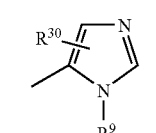

(K)

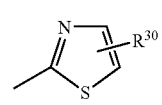

(L)

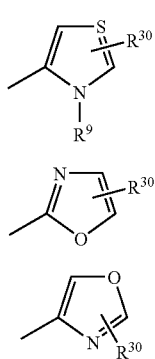

where
R[4] is taken together with the connecting atom in Q to form a double bond as in (C), (D) and (E) or
R[4] and R[9] are independently selected from hydrogen, cyano, nitro, arylalkyl, 2-oxazoline, 2-thiazoline, 2-imidazoline, —C(X)R[10], —C(X)OR[11], —C(X)SR[11], —S(O)$_n$R[11], —C(X)NR[12]R[13], —S(O)$_n$NR[12]R[13], —P(X)(OR[14])(OR[15]), —P(X)(NR[16]R[17])(NR[18]R[19]), —CHR[20]—X—R[21], —CH=NR[22] and —C(=NR[31])(SR[32]);
where X is oxygen or sulfur; R[10] is hydrogen or alkyl; R[11] is hydrogen, alkyl, haloalkyl, hydroxyalkyl, hydroxycarbonylalkyl, alkoxycarbonylalkyl, or —NR[10]CO$_2$R[10]; R[12] and R[13] are independently selected from hydrogen, alkyl, haloalkyl, cycloalkyl, cyanoalkyl, aryl, alkylcarbonyl, alkoxycarbonyl, alkoxycarbonylalkyl, alkoxyalkyl, alkylthioalkyl, alkylsulfinylalkyl, alkylsulfonylalkyl, mono or dialkylaminocarbonylalkyl, aminoalkyl, mono or dialkylaminoalkyl and arylcarbonyl; R[14] and R[15] are independently selected from hydrogen, alkyl and haloalkyl; R[16], R[17], R[18] and R[19] are independently selected from hydrogen and alkyl; R[20] is hydrogen or alkyl; R[21] is alkyl, haloalkyl, —C(X)R[23] or —P(X)(OR[24])(OR[25]); R[22] is hydrogen, alkyl, haloalkyl, hydroxy, alkoxy, haloalkoxy, cyano, pyridinyl or 2-thiazolinyl; R[23] is hydrogen, alkyl or haloalkyl; R[24] and R[25] are independently selected from hydrogen, alkyl and haloalkyl; R[31] and R[32] are independently selected from hydrogen, alkyl, arylalkyl, —C(X)R[10], —CO$_2$R[11], —S(O)$_n$R[11], —C(X)NR[12]R[13], —S(O)$_n$NR[12]R[13], —P(X)(OR[14])(OR[15]), —P(X)(NR[16]R[17])(NR[18]R[19]) and —CHR[20]—X—R[21];

R[5] is selected from hydrogen, halogen, hydroxy, alkyl, alkoxy, alkylthio, haloalkyl, haloalkoxy, aryl, cyano and nitro;
R[6] is selected from hydrogen, halogen, hydroxy, alkyl, alkoxy, alkylthio, haloalkyl, haloalkoxy, aryl, cyano and nitro;
R[7] is hydrogen or alkyl;
R[8] is hydrogen, halogen, alkyl, alkoxy or aryl;
R[30] is hydrogen, halogen or alkyl;
and
agriculturally acceptable salts thereof.

One skilled in the art will, of course, recognize that within the description set forth above, when A is selected from —, —O—, —S(O)$_n$—, —NR[8]—, —CHR[6]O— and —CHR[6]S(O)$_n$— then B is not selected from —O— or —S(O)$_n$—.

The present invention is also directed to compositions containing an insecticidally effective amount of at least one of a compound of formula I, and optionally, an effective amount of at least one of a second compound, with at least one agriculturally acceptable extender or adjuvant.

The present invention is also directed to methods of controlling insects, where control is desired, which comprise applying an insecticidally effective amount of the above composition to the locus of crops, or other areas where insects are present or are expected to be present. Other aspects of the present invention will become apparent.

More specifically, preferred species of this invention are those insecticidal compositions comprised of compounds of formula I
where
A is —CHR[5]—, —CHR[5]CHR[6]— or —OCHR[5]—;
B is —CHR[8]—;
R, R[1], R[2] and R[3] are independently selected from hydrogen, halogen, alkyl and alkoxy;
Q is selected from (C), (D), (E), (F), (G) and (H);
where
R[4] is taken together with the connecting atom in Q to form a double bond as in (C), (D) and (E); or
R[4] is hydrogen;
R[9] is —C(X)R[10], —C(X)OR[11], —C(X)SR[11], —C(X)NR[12]R[13], —P(X)(OR[14])(OR[15]) or —P(X)(NR[16]R[17])(NR[18]R[19]);
where R[10] is alkyl; R[11] is alkyl; R[12] and R[13] are independently selected from hydrogen, alkyl, alkoxyalkyl and alkoxycarbonylalkyl; R[14] and R[15] are independently selected from hydrogen and alkyl;
R[5] is selected from hydrogen, halogen and alkyl;
R[6] is selected from hydrogen, halogen and alkyl;
R[8] is hydrogen, halogen or alkyl; and
R[30] is hydrogen.

More preferred species in this aspect of the invention are those insecticidal compositions comprised of compounds of formula I
where
A is —CHR[5]— or —CHR[5]CHR[6]—;
R is halogen, alkyl or alkoxy;
R[1], R[2] and R[3] are independently selected from hydrogen and halogen;
Q is (c);
R[9] is —C(X)NR[12]R[13] or —P(X)(OR[14])(OR[15]) or P(X)(NR[16]R[17])NR[18]R[19];
where; R[12] and R[13] are independently selected from alkyl, alkoxyalkyl and alkoxycarbonylalkyl; R[14] and R[15] are independently selected from alkyl;
R[16], R[17], R[18], R[19] are independently selected from alkyl;
R[5] is hydrogen;
R[6] is hydrogen; and
R[8] is hydrogen.

Certain of the substituted amino heterocyclic and heteroaryl derivatives described herein are novel compounds. These compounds are represented by formula I:

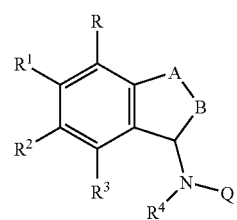

wherein

A is —CHR$^5$—, —CHR$^5$CHR$^6$—, —O—, —S(O)$_n$—, —NR$^7$—, —OCHR$^5$—, —CHR$^5$O—, —S(O)$_n$CHR$^5$—, —CHR$^5$S(O)$_n$—, —C(O)—, —C(S)— or —C(=NOR$^7$)—;

B is —CHR$^8$—, —O— or —S(O)$_n$—;

n is an integer selected from 0, 1 and 2;

R, R$^1$, R$^2$ and R$^3$ are independently selected from hydrogen, halogen, hydroxy, alkyl, alkoxy, haloalkyl, haloalkoxy, haloalkylthio, alkenyl, haloalkenyl, alkynyl, haloalkynyl, cyano, nitro, aryl, aryloxy, heteroaryl, alkoxyalkyl, alkoxyalkoxyalkyl, cycloalkyl, cyanoalkyl, formal, alkoxycarbonyl, acetyl, alkylcarbonyl, alkenylcarbonyl, dialkylphosphonato, SF$_5$, amino, mono- and dialkylamino, cycloalkylamino, (cycloalkyl)(alkyl)amino, alkylthio, sulfonyl, alkylsulfonyl, haloalkylsulfonyl, alkylsulfinyl, alkylsulfinylalkyl, alkylsulfonylalkyl, alkylthiocarbonyl and hydroxycarbonyl;

Q is selected from:

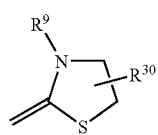
(D)

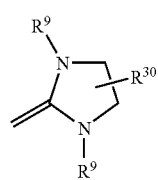
(E)

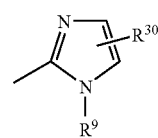
(J)

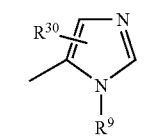
(K)

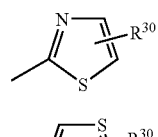
(L)

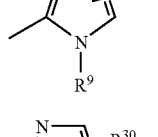
(M)

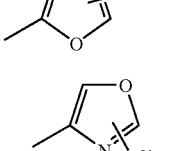
(N)

(O)

where
R$^4$ is taken together with the connecting atom in Q to form a double bond as in (D) and (E) or R$^4$ and R$^9$ are independently selected from hydrogen, cyano, nitro, arylalkyl, 2-oxazoline, 2-thiazoline, 2-imidazoline, —C(X)R$^{10}$, —C(X)OR$^{11}$, —C(X)SR$^{11}$, —S(O)$_n$R$^{11}$, —C(X)NR$^{12}$R$^{13}$, —S(O)$_n$NR$^{12}$R$^{13}$, —P(X)(OR$^{14}$)(OR$^{15}$), —P(X)(NR$^{16}$R$^{17}$)(NR$^{18}$R$^{19}$), —CHR$^{20}$—X—R$^{21}$, —CH=NR$^{22}$ and —C(=NR$^{31}$)(SR$^{32}$);

where X is oxygen or sulfur; R$^{10}$ is hydrogen or alkyl; R$^{11}$ is hydrogen, alkyl, haloalkyl, hydroxyalkyl, hydroxycarbonylalkyl, alkoxycarbonylalkyl, or —NR$^{10}$CO$_2$R$^{10}$; R$^{12}$ and R$^{13}$ are independently selected from hydrogen, alkyl, haloalkyl, cycloalkyl, cyanoalkyl, aryl, alkylcarbonyl, alkoxycarbonyl, alkoxycarbonylalkyl, alkoxyalkyl, alkylthioalkyl, alkylsulfinylalkyl, alkylsulfonylalkyl, mono or dialkylaminocarbonylalkyl, aminoalkyl, mono or dialkylaminoalkyl and arylcarbonyl; R$^{14}$ and R$^{15}$ are independently selected from hydrogen, alkyl and haloalkyl; R$^{16}$, R$^{17}$, R$^{18}$ and R$^{19}$ are independently selected from hydrogen and alkyl; R$^{20}$ is hydrogen or alkyl; R$^{21}$ is alkyl, haloalkyl, —C(X)R$^{23}$ or —P(X)(OR$^{24}$)(OR$^{25}$); R$^{22}$ is hydrogen, alkyl, haloalkyl, hydroxy, alkoxy, haloalkoxy, cyano, pyridinyl or 2-thiazolinyl; R$^{23}$ is hydrogen, alkyl or haloalkyl; R$^{24}$ and R$^{25}$ are independently selected from hydrogen, alkyl and haloalkyl; R$^{31}$ and R$^{32}$ are independently selected from hydrogen, alkyl, arylalkyl, —C(X)R$^{10}$, —CO$_2$R$^{11}$, —S(O)$_n$R$^{11}$, —C(X)NR$^{12}$R$^{13}$, —S(O)$_n$NR$^{12}$R$^{13}$, —P(X)(OR$^{14}$)(OR$^{15}$), —P(X)(NR$^{16}$R$^{17}$)(NR$^{18}$R$^{19}$) and —CHR$^{20}$—X—R$^{21}$;

R$^5$ is selected from hydrogen, halogen, hydroxy, alkyl, alkoxy, alkylthio, haloalkyl, haloalkoxy, aryl, cyano and nitro;

R$^6$ is selected from hydrogen, halogen, hydroxy, alkyl, alkoxy, alkylthio, haloalkyl, haloalkoxy, aryl, cyano and nitro;

R$^7$ is hydrogen or alkyl;

R$^8$ is hydrogen, halogen, alkyl, alkoxy or aryl;

R$^{30}$ is hydrogen, halogen or alkyl;

and agriculturally acceptable salts thereof.

Other novel substituted amino heterocyclic and heteroaryl derivatives described herein are represented by formula I:

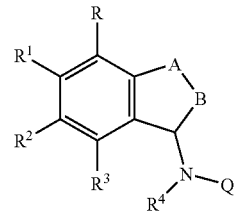

I wherein

A is —CHR$^5$—, —CHR$^5$CHR$^6$—, —O—, —S(O)$_n$—, —NR$^7$—, —OCHR$^5$—, —CHR$^5$O—, —S(O)$_n$CHR$^5$—, —CHR$^5$S(O)$_n$—, —C(O)—, —C(S)— or —C(=NOR$^7$)—;

B is —CHR$^8$—, —O— or —S(O)$_n$—;

n is an integer selected from 0, 1 and 2;

R, R$^1$, R$^2$ and R$^3$ are independently selected from hydrogen, halogen, hydroxy, alkyl, alkoxy, haloalkyl, haloalkoxy, haloalkylthio, alkenyl, haloalkenyl, alkynyl, haloalkynyl, cyano, nitro, aryl, aryloxy, heteroaryl, alkoxyalkyl, alkoxyalkoxyalkyl, cycloalkyl, cyanoalkyl, formal, alkoxycarbonyl, acetyl, alkylcarbonyl, alkenylcarbonyl, dialkylphosphonato, SF₅, amino, mono- and dialkylamino, cycloalkylamino, (cycloalkyl)(alkyl)amino, alkylthio, sulfonyl, alkylsulfonyl, haloalkylsulfonyl, alkylsulfinyl, alkylsulfinylalkyl, alkylsulfonylalkyl, alkylthiocarbonyl and hydroxycarbonyl;

Q is:

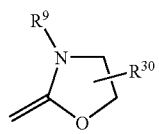

(C)

where

R$^4$ is taken together with the connecting atom in Q to form a double bond;

R$^9$ is selected from hydrogen, cyano, nitro, arylalkyl, 2-oxazoline, 2-thiazoline, 2-imidazoline, —C(X)R$^{10}$, —C(X)OR$^{11}$, —C(X)SR$^{11}$, —S(O)$_n$R$^{11}$, —C(X)NR$^{12}$R$^{13}$, —S(O)$_n$NR$^{12}$R$^{13}$, —P(X)(OR$^{14}$)(OR$^{15}$), —P(X)(NR$^{16}$R$^{17}$)(NR$^{18}$R$^{19}$), —CHR$^{20}$—X—R$^{21}$, —CH=NR$^{22}$ and —C(=NR$^{31}$)(SR$^{32}$);

where X is oxygen or sulfur; R$^{10}$ is hydrogen or alkyl; R$^{11}$ is hydrogen, alkyl, haloalkyl, hydroxyalkyl, hydroxycarbonylalkyl, alkoxycarbonylalkyl, or —NR$^{10}$CO$_2$R$^{10}$; R$^{12}$ and R$^{13}$ are independently selected from hydrogen, alkyl, haloalkyl, cycloalkyl, cyanoalkyl, aryl, alkylcarbonyl, alkoxycarbonyl, alkoxycarbonylalkyl, alkoxyalkyl, alkylthioalkyl, alkylsulfinylalkyl, alkylsulfonylalkyl, mono or dialkylaminocarbonylalkyl, aminoalkyl, mono or dialkylaminoalkyl and arylcarbonyl; R$^{14}$ and R$^{15}$ are independently selected from hydrogen, alkyl and haloalkyl; R$^{16}$, R$^{17}$, R$^{18}$ and R$^{19}$ are independently selected from hydrogen and alkyl; R$^{20}$ is hydrogen or alkyl; R$^{21}$ is alkyl, haloalkyl, —C(X)R$^{23}$ or —P(X)(OR$^{24}$)(OR$^{25}$); R$^{22}$ is hydrogen, alkyl, haloalkyl, hydroxy, alkoxy, haloalkoxy, cyano, pyridinyl or 2-thiazolinyl; R$^{23}$ is hydrogen, alkyl or haloalkyl; R$^{24}$ and R$^{25}$ are independently selected from hydrogen, alkyl and haloalkyl; R$^{31}$ and R$^{32}$ are independently selected from hydrogen, alkyl, arylalkyl, —C(X)R$^{10}$, —CO$_2$R$^{11}$, —S(O)$_n$R$^{11}$, —C(X)NR$^{12}$R$^{13}$, —S(O)$_n$NR$^{12}$R$^{13}$, —P(X)(OR$^{14}$)(OR$^{15}$), —P(X)(NR$^{16}$R$^{17}$)(NR$^{18}$R$^{19}$) and —CHR$^{20}$—X—R$^{21}$;

R$^5$ is selected from hydrogen, halogen, hydroxy, alkyl, alkoxy, alkylthio, haloalkyl, haloalkoxy, aryl, cyano and nitro;

R$^6$ is selected from hydrogen, halogen, hydroxy, alkyl, alkoxy, alkylthio, haloalkyl, haloalkoxy, aryl, cyano and nitro;

R$^7$ is hydrogen or alkyl;

R$^8$ is hydrogen, halogen, alkyl, alkoxy or aryl;

R$^{30}$ is hydrogen, halogen or alkyl;

provided that when R$^9$ is hydrogen then at least one of R, R$^1$, R$^2$ and R$^3$ is other than hydrogen;

and agriculturally acceptable salts thereof.

Additional novel substituted amino heterocyclic and heteroaryl derivatives described herein are represented by formula I:

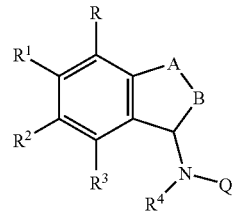

wherein

A is —CHR$^5$—, —CHR$^5$CHR$^6$—, —O—, —S(O)$_n$—, —NR$^7$—, —OCHR$^5$—, —CHR$^5$O—, —S(O)$_n$CHR$^5$—, —CHR$^5$S(O)$_n$—, —C(O)—, —C(S)— or —C(=NOR$^7$)—;

B is —CHR$^8$—, —O— or —S(O)$_n$—;

n is an integer selected from 0, 1 and 2;

R, R$^1$, R$^2$ and R$^3$ are independently selected from hydrogen, halogen, hydroxy, alkyl, alkoxy, haloalkyl, haloalkoxy, haloalkylthio, alkenyl, haloalkenyl, alkynyl, haloalkynyl, cyano, nitro, aryl, aryloxy, heteroaryl, alkoxyalkyl, alkoxyalkoxyalkyl, cycloalkyl, cyanoalkyl, formal, alkoxycarbonyl, acetyl, alkylcarbonyl, alkenylcarbonyl, dialkylphosphonato, SF₅, amino, mono- and dialkylamino, cycloalkylamino, (cycloalkyl)(alkyl)amino, alkylthio, sulfonyl, alkylsulfonyl, haloalkylsulfonyl, alkylsulfinyl, alkylsulfinylalkyl, alkylsulfonylalkyl, alkylthiocarbonyl and hydroxycarbonyl;

Q is selected from:

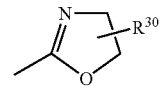

(F)

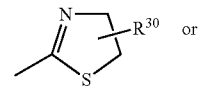

(G)

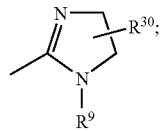

(H)

where

R$^4$ and R$^9$ are independently selected from hydrogen, cyano, nitro, arylalkyl, 2-oxazoline, 2-thiazoline, 2-imidazoline, —C(X)R$^{10}$, —C(X)OR$^{11}$, —C(X)SR$^{11}$, —S(O)$_n$R$^{11}$, —C(X)NR$^{12}$R$^{13}$, S(O)$_n$NR$^{12}$R$^{13}$, —P(X)(OR$^{14}$)(OR$^{15}$), —P(X)(NR$^{16}$R$^{17}$)(NR$^{18}$R$^{19}$), —CHR$^{20}$—X—R$^{21}$, —CH=NR$^{22}$ and —C(=NR$^{31}$)(SR$^{32}$);

where X is Oxygen or sulfur; R$^{10}$ is hydrogen or alkyl; R$^{11}$ is hydrogen, alkyl, haloalkyl, hydroxyalkyl, hydroxycarbonylalkyl, alkoxycarbonylalkyl, or —NR$^{10}$CO$_2$R$^{10}$; R$^{12}$ and R$^{13}$ are independently selected from hydrogen, alkyl, haloalkyl, cycloalkyl, cyanoalkyl, aryl, alkylcarbonyl, alkoxycarbonyl, alkoxycarbonylalkyl, alkoxyalkyl, alkylthioalkyl, alkylsulfinylalkyl, alkylsulfonylalkyl, mono or dialkylaminocarbonylalkyl, aminoalkyl, mono or dialkylaminoalkyl and arylcarbonyl; R$^{14}$ and R$^{15}$ are independently selected from hydrogen, alkyl and haloalkyl; R$^{16}$, R$^{17}$, R$^{18}$ and R$^{19}$ are independently selected from hydrogen and alkyl; $R^{20}$ is hydrogen or alkyl; $R^{21}$ is alkyl, haloalkyl, —C(X)$R^{23}$ or —P(X)(O$R^{24}$)(O$R^{25}$); $R^{22}$ is hydrogen, alkyl, haloalkyl, hydroxy, alkoxy, haloalkoxy, cyano, pyridinyl or 2-thiazolinyl; $R^{23}$ is hydrogen, alkyl or haloalkyl; $R^{24}$ and $R^{25}$ are independently selected from hydrogen, alkyl and haloalkyl; $R^{31}$ and $R^{32}$ are independently selected from hydrogen, alkyl, arylalkyl, —C(X)$R^{10}$, —CO$_2R^{11}$, —S(O)$_nR^{11}$, —C(X)N$R^{12}R^{13}$, —S(O)$_n$N$R^{12}R^{13}$, —P(X)(O$R^{14}$)(O$R^{15}$), —P(X)(N$R^{16}R^{17}$)(N$R^{18}R^{19}$) and —CH$R^{20}$—X—$R^{21}$;

$R^5$ is selected from hydrogen, halogen, hydroxy, alkyl, alkoxy, alkylthio, haloalkyl, haloalkoxy, aryl, cyano and nitro;

$R^6$ is selected from hydrogen, halogen, hydroxy, alkyl, alkoxy, alkylthio, haloalkyl, haloalkoxy, aryl, cyano and nitro;

$R^7$ is hydrogen or alkyl;

$R^8$ is hydrogen, halogen, alkyl, alkoxy or aryl;

$R^{30}$ is hydrogen, halogen or alkyl;

provided that i) when A is —CH$R^5$— or —CH$R^5$CH$R^6$—, B is —CH$R^8$—, R, $R^1$, $R^2$, $R^3$, $R^5$, $R^6$ and $R^8$ are independently selected from hydrogen, halogen, alkyl, alkoxy, haloalkyl, haloalkoxy or alkylthio then at least one of $R^4$ and $R^9$ is other than hydrogen, and ii) when A is —OCH$R^5$—, —CH$R^5$O—, —S(O)$_n$CH$R^5$— or —CH$R^5$S(O)$_n$—, B is —CH$R^8$—, Q is (F), R, $R^1$, $R^2$ and $R^3$ are independently selected from hydrogen, halogen, alkyl, alkoxy, alkylthio and dialkylamino, $R^5$ and $R^8$ are independently selected from hydrogen and alkyl, then $R^4$ is other than hydrogen;

and agriculturally acceptable salts thereof.

The present invention is also directed to certain novel substituted ethyl carboxamide and thiocarboxamide intermediates, useful in preparing the compounds of the present invention, represented by formula IA:

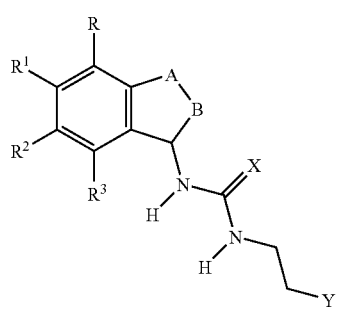

IA wherein

A is —CH$R^5$—, —CH$R^5$CH$R^6$—, —O—, —S(O)$_n$—, —N$R^7$—, —OCH$R^5$—, —CH$R^5$O—, —S(O)$_n$CH$R^5$—, —CH$R^5$S(O)$_n$—, —C(O)—, —C(S)— or —C(=N O$R^7$)—;

B is —CH$R^8$—, —O— or —S(O)$_n$—;

N is an integer selected from 0, 1 and 2;

R, $R^1$, $R^2$ and $R^3$ are independently selected from hydrogen, halogen, hydroxy, alkyl, alkoxy, haloalkyl, haloalkoxy, haloalkylthio, alkenyl, haloalkenyl, alkynyl, haloalkynyl, cyano, nitro, aryl, aryloxy, heteroaryl, alkoxyalkyl, alkoxyalkoxyalkyl, cycloalkyl, cyanoalkyl, formal, alkoxycarbonyl, acetyl, alkylcarbonyl, alkenylcarbonyl, dialkylphosphonato, SF$_5$, amino, mono- and dialkylamino, cycloalkylamino, (cycloalkyl)(alkyl)amino, alkylthio, sulfonyl, alkylsulfonyl, haloalkylsulfonyl, alkylsulfinyl, alkylsulfinylalkyl, alkylsulfonyl-alkyl, alkylthiocarbonyl and hydroxycarbonyl;

X is oxygen or sulfur; and

Y is chlorine, bromine, iodine, methanesulfonyloxy or p-toluenesulfonyloxy;

provided that when A is —O—, —CH$R^5$— or —CH$R^5$CH$R^6$—, B is —CH$R^8$—, where $R^5$, $R^6$ and $R^8$ are selected from hydrogen, alkyl, alkoxy, alkylthio, chlorine, bromine or iodine and X is oxygen then at least one of R, $R^1$, $R^2$ and $R^3$ is other than hydrogen, alkyl, alkoxy, alkylthio, chlorine, bromine or iodine.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties.

The compounds of the present invention may exist as tautomers, in which migration of a hydrogen atom within the molecule results in two or more structures, which are in equilibrium. For example, compounds of formula I wherein Q is selected from (C), (D), (E), (F), (G) or (H) may exist in tautomeric forms as shown in formulae Ia and Ib. Such tautomerism is well known as is described in S. Patai (The Chemistry of Functional Groups: Amidines and Imidates, Vol 2, 1991, pages 259-262). It will be understood that all such tautomeric forms are embraced by the present invention.

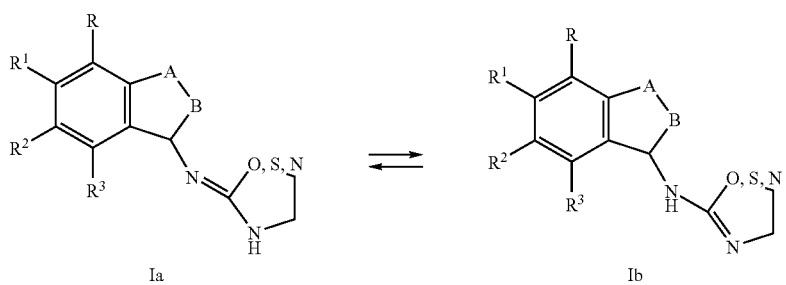

This invention includes the use of such enantiomorphs, polymorphs, tautomers, salts and metal complexes. The compounds of the present invention may also possess acidic or basic moieties, which may allow for the formation of agriculturally acceptable salts or agriculturally acceptable metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I with at least one insecticidally compatible carrier therefor.

Another aspect of the present invention relates to compositions containing an insecticidally effective amount of at least one compound of formula I, and an effective amount of at least one additional compound, with at least one insecticidally compatible carrier therefor.

Another aspect of the present invention relates to methods of controlling insects by applying an insecticidally effective amount of a composition set forth above to a locus of crops such as, without limitation, cereals, cotton, vegetables, and fruits, or other areas where insects are present or are expected to be present.

Another aspect of the present invention relates to novel intermediates finding utility in the syntheses of compounds of formula I.

The present invention also includes the use of the compounds and compositions set forth herein for control of non-agricultural insect species, for example, dry wood termites, subterranean termites and general household pests; as well as for use as pharmaceutical agents and compositions thereof. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "cycloalkyl", used alone or as part of a larger moiety, includes cyclic rings of at least three carbon atoms and up to eight carbon atoms, more preferably three to six carbon atoms. The terms "haloalkyl" and "haloalkoxy" used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms, wherein one or more hydrogen atoms have been replaced with halogen atoms, for example, trifluoromethyl or 2,2,2-trifluoroethoxy. The term "aryl" refers to an aromatic ring structure, including fused rings, having four to ten carbon atoms, for example, phenyl, indanyl, indenyl, naphthyl or 5,6,7,8-tetrahydronaphthyl. The term "heteroaryl" refers to an aromatic ring structure, including fused rings, in which at least one of the atoms is other than carbon, for example, without limitation, sulfur, oxygen, or nitrogen. Heteroaryl rings include, without limitation, for example, oxazolyl, thiazolyl, imidazolyl, pyrazolyl, triazolyl or thiadiazolyl. The term "DMF" refers to N,N-dimethylformamide. The term "THF" refers to tetrahydrofuran. The term "DBU" refers to 1,8-diazabicyclo[5.4.0]undec-7-ene. The term "halogen" or "halo" refers to fluorine, bromine, iodine, or chlorine. The term "ambient temperature", for example, in reference to a chemical reaction mixture temperature, refers to a temperature in the range of 20° C. to 30° C. The terms "insecticidal", "acaricidal", "insecticide" or "acaricide" refer to a compound of the present invention, either alone or in admixture with at least one additional compound, or with at least one compatible carrier, which causes the destruction or the inhibition of action of insects or acarids. The term "general household pest" refers to any insect or pest, such as German cockroach, American cockroach, Smokey-Brown cockroach, Oriental cockroach, house fly, biting fly, filth fly, red imported fire ant (RIFA), odorous house ant, carpenter ant, pharaoh ant, termite, Argentine ant, mosquito, tick, flea, sowbug, pillbug, centipede, spider, silverfish, scorpion and bedbug, that cause harm or nuisance to person or property.

The compounds of the present invention were prepared by methods generally known to those skilled in the art. A number of the compounds of the present invention were prepared in the manner shown in Scheme 1.

Scheme 1

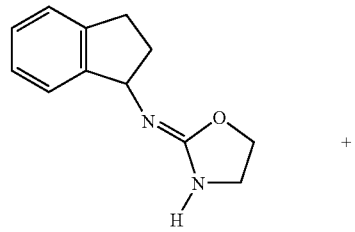

(SM1)
where A is —CHR$^5$—, B is —CHR$^8$—,
R, R$^1$, R$^2$, R$^3$, R$^5$ and R$^8$ are hydrogen
and Q is (C)

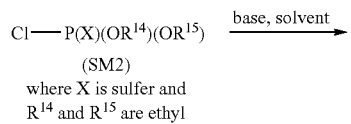

Cl—P(X)(OR$^{14}$)(OR$^{15}$) $\xrightarrow{\text{base, solvent}}$ (SM2)
where X is sulfer and
R$^{14}$ and R$^{15}$ are ethyl

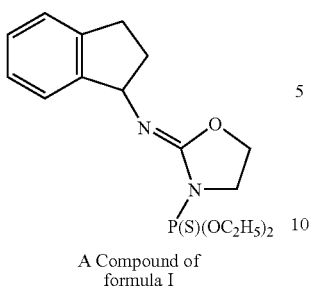

A Compound of
formula I

As depicted in Scheme 1, the reaction of a 1,3-oxazolidine (SM1), for example 2-(azaindanylmethylene)-1,3-oxazolidine (known compound, Offenlegungsschrift 1,963,192) and diethylchlorothiophosphonate (SM2) yielded the appropriately substituted 1,3-oxazolinyl phosphino thione, for example, (2-(azaindanylmethylene)(1,3-oxazolidin-3-yl)diethylphosphino-1-thione, a compound of formula I described in detail in Example 1 set forth below.

Scheme 2 provides a general method for the preparation of compounds of formula I in which the Q substituent is (C).

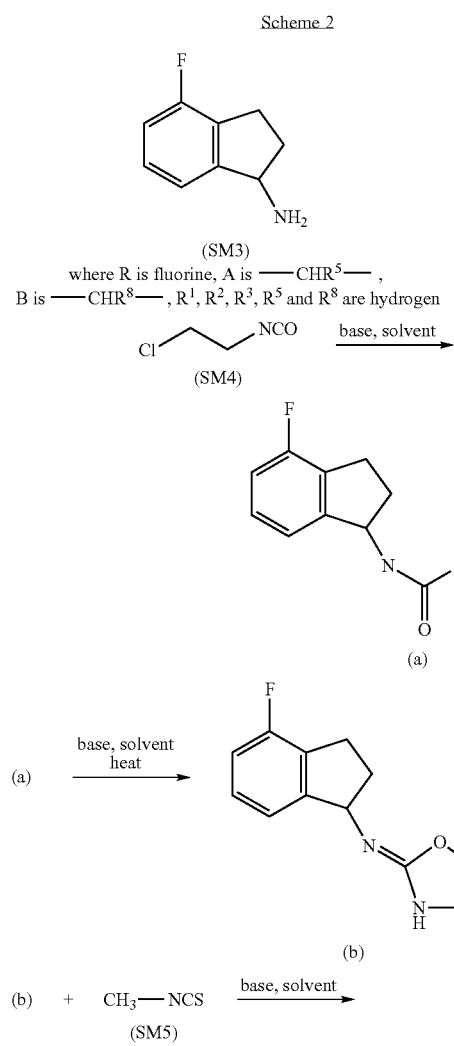

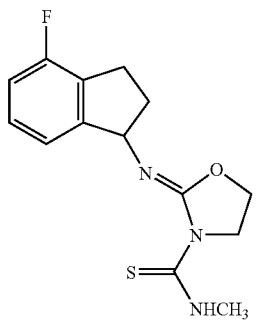

A Compound of
formula I

As depicted in Scheme 2, the reaction of an appropriately substituted indanyl amine, for example 4-fluoroindanylamine (known compound, U.S. Pat. No. 5,486,541) with 2-chloroethyl isocyanate (SM4) under basic conditions, in an appropriate solvent yielded the corresponding indanyl carboxamide intermediate (a), for example, [(2-chloroethyl)amino]-N-(4-fluoroindanyl)carboxamide. Intermediate (a) was heated under basic conditions in an appropriate solvent to yield the appropriate indanyl 1,3-oxazolidine, a compound of formula I and an intermediate (b), for example, 2-[aza(4-fluoroindanyl)methylene]-1,3-oxazolidine, described in detail in Example 2, Step B, as set forth below. Compound (b) was reacted with an isothiocyanate, for example, methyl isothiocyanate, under basic conditions yielding the corresponding amino methane-1-thione, for example, 2-[aza(4-fluoroindanyl)methylene](1,3-oxazolidin-3-yl)(methylamino)methane-1-thione, a compound of formula I, described in detail in Example 2, Step C, as set forth below.

Scheme 3 provides an alternative method for the preparation of compounds of formula I.

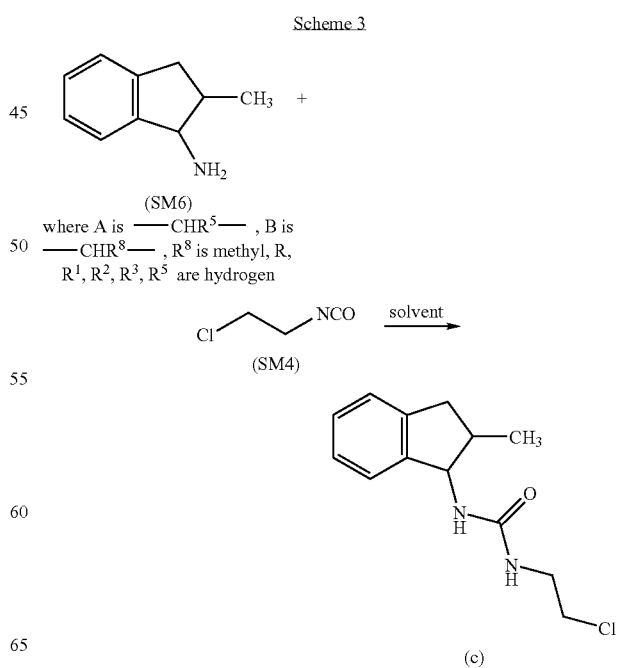

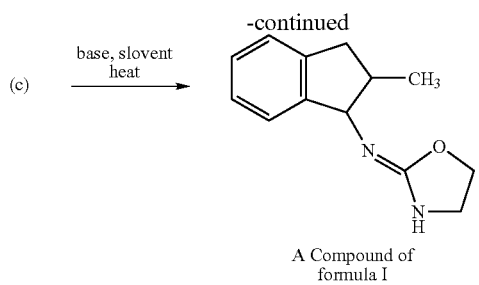

A Compound of formula I

As depicted in Scheme 3, the reaction of a substituted indanyl amine (SM6), for example, 2-methylindanylamine (known compound, JCS, Transactions (1919), 115, 61-67) and 2-chloroethyl isocyanate (SM4) in an appropriate solvent yielded the appropriately substituted indanyl carboxamide intermediate (c), for example, [(2-chloroethyl)amino]-N-(2-methylindanyl)carboxamide. Heating intermediate (c) with a base in an appropriate solvent produced the corresponding substituted indanyl 1,3-oxazolidine, for example, 2-[aza(2-methylindanyl)methylene]-1,3-oxazolidine, a compound of formula I described in detail in Example 3 set forth below.

Scheme 4 provides another general method for the preparation of compounds of formula I.

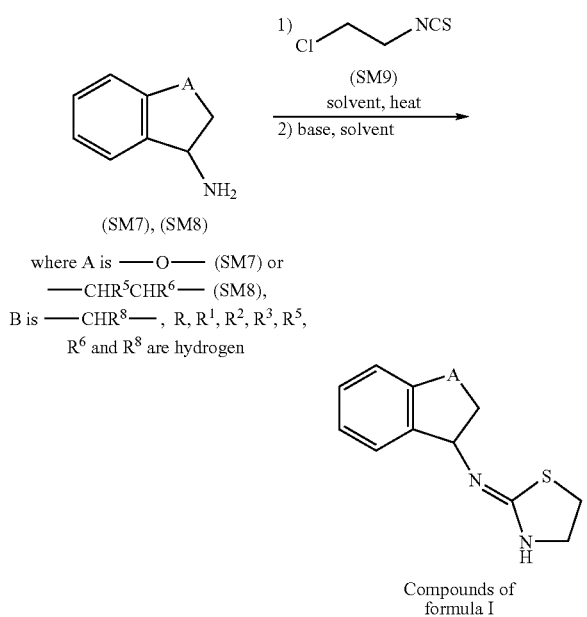

Compounds of formula I

As depicted in Scheme 4, the reaction of a 2,3-dihydrobenzo[b]furan-3-ylamine (SM7) or a 1, 2, 3, 4-tetrahydronaphthylamine (SM8) first with 2-chloroethyl isothiocyanate in an appropriate solvent forming an intermediate 2-chloroethyl thiocarboxamide, and second, stirring the intermediate in a solvent under basic conditions yielded compounds of formula I, for example, when A is —O—, 2-(aza-2,3-dihydrobenzo[b]furan-3-ylmethylene)-1,3-thiazolidine or when A is —$CHR^5CHR^6$—, 2-(aza-1,2,3,4-tetrahydronaphthylmethylene)-1,3-thiazolidine. These compounds of formula I are described in detail in Examples 4 and 5 respectively set forth below.

One skilled in the art will, of course, recognize that the formulation and mode of application of a toxicant may affect the activity of the material in a given application. Thus, for agricultural and general household pest use the present insecticidal compounds may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agents and/or oils will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

For veterinary use of the compounds of the invention in domestic and non-domestic animals, the compounds may be administered alone or in a formulation appropriate to the specific use envisaged and to the particular species of host animal being treated and the pest involved. The methods by which the compounds may be administered include oral administration by capsule, bolus, tablet or drench, or as a pour-on or spot-on formulation, or alternatively, they can be administered by injection (e.g. subcutaneously, intramuscularly or intravenously), dip, spray, mousse, shampoo, powder, or as an implant.

Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. Oral drenches are prepared by dissolving or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolving or suspending the active ingredient in the liquid carrier such that the final formulation contains from 0.01 to 10% by weight of the active ingredient.

These formulations will vary with regard to the weight of active compound contained therein depending on the species of host animal to be treated, the severity and type of infection and the body weight of the host. For parenteral, topical (e.g. using pour-on or spot-on, dip, spray, mousse, shampoo or powder to deliver the compound) and oral administration, typical dose ranges of the active ingredient are 0.01-100 mg per kg of body weight of the animal. Preferably the range is 0.1 to 10 mg per kg.

As an alternative the compounds may be administered with the animal feedstuff and for this purpose a concentrated feed additive or premix may be prepared for mixing with the normal animal feed.

The compounds of the invention may, in particular, be used in the field of veterinary medicine and livestock husbandry against arthropods, helminths or protozoa which are parasitic internally or externally upon vertebrates, particularly warm-blooded vertebrates, for example domestic and non-domestic animals, e.g. cattle, sheep, goats, equines, swine, poultry, dogs, and cats. The compounds of the invention may be particularly useful in controlling arthropods, helminths or protozoa which are present inside the host animals or which feed in or on the skin or suck the blood of the animal, for which purpose they may be administered orally, parenterally, percutaneously or topically.

According to a further aspect of the invention, there is provided a pesticidal formulation comprising a compound of the invention, in admixture with a compatible adjuvant, diluent or carrier. Preferably, the formulation is adapted for topical administration.

The invention further provides a compound of the invention for use as a pesticide; and a method of treating a pest infestation at a locus, which comprises treatment of the locus with an effective amount of a compound of the invention. Preferably, the locus is the skin or fur of an animal.

The active insecticidal compounds of this invention may be formulated and/or applied with one or more additional compound. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Additional compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with at least one additional compound, e.g., with other pesticides such as herbicides, the herbicides include, without limitation, for example: N-(phosphonomethyl)glycines such as glyphosate; aryloxyalkanoic acids such as 2,4-D, MCPA, and MCPP; ureas such as isoproturon; imidazolinones such as imazapyr, imazamethabenz, imazethapyr, and imazaquin; diphenyl ethers such as acifluorfen, bifenox, and fomasafen; hydroxybenzonitriles such as ioxynil and bromoxynil; sulfonylureas such as chlorimuron, achlorsulfuron, bensulfuron, pyrazosulfuron, thifensulfuron, and triasulfuron; 2-(4-aryloxyphenoxy)alkanoic acids such as fenoxaprop, fluazifop, quizalofop, and diclofop; benzothiadiazinones such as bentazone; 2-chloroacetanilides such as butachlor, metolachlor, acetochlor, and dimethenamide; arenecarboxylic acids such as dicamba; pyridyloxyacetic acids such as fluoroxypyr, aryl triazolinones such as sulfentrazone and carfentrazone-ethyl; isoxazolidinones such as clomazone; and other herbicides.

When the active insecticidal compounds of the present invention are used in combination with at least one additional compound, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, beta-cypermethrin, zeta-cypermethrin, bifenthrin, cypermethrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, imidacloprid, and other insecticides.

When the active insecticidal compounds of the present invention are used in combination with one or more of an additional compound, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with at least one additional compound, e.g., with other pesticides such as nematicides, the nematicides include, for example: carbofuran, carbosulfan, terbufos, aldecarb, ethoprop, fenamphos, oxamyl, isazofos, cadusafos, and other nematicides.

When the active insecticidal compounds of the present invention are used in combination with one or more of an additional compound, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne cyanobacteria.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The compounds of formula I can be synthesized by methods that are individually known to one skilled in the art from intermediate compounds readily available in commerce.

Example 1

This Example Illustrates One Protocol for the Preparation of [2-(azaindanylmethylene)(1,3-oxazolidin-3-yl)]diethoxyphosphino-1-thione (Compound 1-2)

To a cold (0° C.) mixture of 0.4 gram (0.0019 mole) of 2-(azaindanylmethylene)-1,3-oxazolidine (known compound) and 0.8 gram (0.006 mole) of N,N-diisopropylethylamine in 20 mL of methylene chloride was added 0.32 gram (0.002 mole) of diethylchlorothiophosphonate. The reaction mixture was allowed to warm to ambient temperature and stir for about 18 hours. The reaction mixture was concentrated under reduced pressure to leave a residue. The residue was diluted with diethyl ether and filtered. The filtrate was concentrated under reduced pressure to leave a residue. The residue was purified by column chromatography on basic alumina, eluting with methylene chloride. The appropriate fractions were combined and concentrated under reduced pressure to yield 0.38 gram of [2-(azaindanylmethylene)(1,3-oxazolidin-3-yl)]diethoxyphosphino-1-thione (Compound 1-2) as an oil. The NMR spectrum was consistent with the proposed structure.

Example 2

This Example Illustrates One Protocol for the Preparation of 2-[aza(4-fluoroindanyl)methylene]-1,3-oxazolidine (Compound 1-21) and {2-[aza(4-fluoroindanyl)methylene](1,3-oxazolidin-3-yl)}(methylamino)methane-1-thione (Compound 1-27)

Step A Preparation of [(2-chloroethyl)amino]-N-(4-fluoroindanyl)carboxamide as an Intermediate To a stirred, cold (0° C.) solution of 7.0 grams (0.046 mole) of 4-fluoroindanylamine (known compound) and 5.7 grams (0.056 mole) of triethylamine in 100 mL of methylene chloride was added 5.4 grams (0.051 mole) of 2-chloroethyl isocyanate. The cold reaction mixture was stirred for three hours at which time it was filtered. The filter cake was rinsed with methylene chloride. The filtrates were combined and concentrated under reduced pressure to a residue. The residue was triturated with hexanes and the mixture filtered. The filter cake was dried under reduced pressure to yield 4.0 grams of [(2-chloroethyl)amino]-N-(4-fluoroindanyl)carboxamide. The NMR spectrum was consistent with the proposed structure.

Step B Preparation of
2-[aza(4-fluoroindanyl)methylene]-1,3-oxazolidine
(Compound 1-21)

To a stirred solution of 4.0 grams (0.016 mole) of [(2-chloroethyl)amino]-N-(4-fluoroindanyl)carboxamide in 40 mL of acetonitrile was added 3.1 grams (0.02 mole) of DBU. The reaction mixture was heated at 45° C. where it stirred for about 18 hours. The reaction mixture was concentrated under reduced pressure to a residue. The residue was dissolved in 100 mL of ethyl acetate and extracted with three 30 mL portions of water. The washed organic phase was dried with sodium sulfate, filtered and the filtrate concentrated to a residue. This residue was purified by column chromatography on basic alumina, eluted with mixtures of methylene chloride and methanol. The appropriate fractions were combined and concentrated under reduced pressure to leave a solid. The solid was triturated with hexanes, filtered and the filter cake dried under reduced pressure to yield 1.7 grams of 2-[aza(4-fluoroindanyl)methylene]-1,3-oxazolidine, Compound 1-21, as a solid. Another sample of Compound 1-21, prepared in the same manner as Example 2, Steps A and B, had a melting point of 93-94° C. The NMR spectrum was consistent with the proposed structure.

Step C Preparation of {2-[aza(4-fluoroindanyl)methylene](1,3-oxazolidin-3-yl)}(methylamino)methane-1-thione (Compound 1-27)

To a stirred solution of 0.3 gram (0.0014 mole) of 2-[aza (4-fluoroindanyl)methylene]-1,3-oxazolidine (Compound 1-21) and 0.1 gram (0.0014 mole) of methyl isothiocyanate was added 0.21 gram (0.0013 mole) of diisopropylethylamine. The reaction mixture stirred for three hours at which time it was concentrated under reduced pressure to leave a residue. The residue was purified by column chromatography on silica gel eluting with methylene chloride. The appropriate fractions were combined and concentrated to yield 0.3 gram of {2-[aza(4-fluoroindanyl)methylene](1,3-oxazolidin-3-yl) }(methylamino)methane-1-thione, Compound 1-27, as a solid, melting point 146-147° C. The NMR spectrum was consistent with the proposed structure.

Example 3

This example illustrates one protocol for the preparation of
2-[aza(2-methylindanyl)methylene]-1,3-oxazolidine
(Compound 1-34)

Step A Preparation of [(2-chloroethyl)amino]-N-(2-methylindanyl)carboxamide as an Intermediate To a stirred mixture of 0.9 gram (0.0061 mole) of 2-methylindanylamine (known compound) in 20 mL of diethyl ether was added 0.53 gram (0.0062 mole) of 2-chloroethyl isocyanate. The reaction mixture was stirred for one hour at which time it was filtered. The filter cake was rinsed with diethyl ether, then was dried under reduced pressure to yield 1.2 grams of [(2-chloro-ethyl)amino]-N-(2-methylindanyl)carboxamide as a solid, melting point 105-106° C. The NMR spectrum was consistent with the proposed structure.

Step B Preparation of
2-[aza(2-methylindanyl)methylene]-1,3-oxazolidine
(Compound 1-34)

A stirred mixture of 0.5 gram (0.002 mole) of [(2-chloroethyl)amino]-N-(2-methylindanyl)carboxamide in 20 mL of acetonitrile was warmed until a solution formed and 0.33 mL (0.0022 mole) of DBU was added. The reaction mixture was heated at reflux for two hours, allowed to cool to ambient temperature and concentrated under reduced pressure to a residue. The residue was dissolved in 100 mL of ethyl acetate and the solution extracted with three 50 mL portions of water. The organic phase was dried with sodium sulfate, filtered and the filtrate concentrated under reduced pressure to yield 0.43 gram of 2-[aza(2-methylindanyl)methylene]-1,3-oxazolidine, Compound 1-34, as an oil. The NMR spectrum was consistent with the proposed structure.

Example 4

This Example Illustrates One Protocol for the preparation of 2-(aza-2,3-dihydrobenzo[b]furan-3-ylmethylene)-1,3-thiazolidine (Compound 4-1)

A stirred mixture of 0.5 gram (0.0037 mole) of 2,3-dihydrobenzo[b]furan-3-ylamine (known compound, Chimica Acta Turcica (1985), 13(3), 403-412) and 0.036 mL (0.0037 mole) of 2-chloroethlisothiocyanate in 10 mL of 1,4-dioxane was heated at reflux for two hours at which time a precipitate had formed. The reaction mixture was allowed to cool to ambient temperature, was filtered and the filter cake rinsed first with 1,4-dioxane followed by water. The solid was added to a stirred mixture of 5 mL of water and 20 mL of diethyl ether to which 2.0 grams (0.005 mole) of sodium hydroxide was added. The reaction mixture was stirred at ambient temperature until all the solid had gone into solution (about 20 minutes). The reaction mixture was poured into a separatory funnel and the organic phase was separated from the aqueous phase. The organic phase was dried with sodium sulfate, filtered and the filtrate concentrated under reduced pressure to yield 0.52 gram of 2-(aza-2,3-dihydrobenzo[b]furan-3-ylmethylene)-1,3-thiazolidine, Compound 4-1, as an off white solid, melting point 136-137° C. The NMR spectrum was consistent with the proposed structure.

Example 5

This example illustrates one protocol for the preparation of 2-(aza-1,2,3,4-tetrahydronaphthylmethylene)-1,3-thiazolidine (Compound 6-1)

In a manner similar to Example 4, the reaction of 0.34 gram (0.0023 mole) of 1,2,3,4-tetrahydro-1-naphthylamine (Aldrich Chemical Company) and 0.22 mL (0.0023 mole) of 2-chloroethyl isothiocyanate in 5 mL of 1,4-dioxane followed by 0.15 gram (0.0038 mole) of sodium hydroxide in 10 mL of water and 10 mL of diethyl ether provided 0.24 gram of 2-(aza-1,2,3,4-tetrahydronaphthylmethylene)-1,3-thiazolidine, Compound 6-1, as a white solid, melting point 160-162° C. The NMR spectrum was consistent with the proposed structure.

The following table sets forth some additional examples of compounds of formula I useful in the present invention:

TABLE 1

Insecticidal Substituted Amino Heterocyclic Derivatives

I where A is —CHR$^5$—, B is —CHR$^8$—, Q is (C) and R$^{30}$ is hydrogen:

I-1

| Cmpd No. | R | R$^1$ | R$^2$ | R$^3$ | R$^5$ | R$^8$ | R$^9$ |
|---|---|---|---|---|---|---|---|
| 1-1 | H | H | H | H | H | H | —CN |
| 1-2 | H | H | H | H | H | H | —P(S)(OC$_2$H$_5$)$_2$ |
| 1-3 | H | H | H | H | H | H | —C(O)NHCH$_3$ |
| 1-4 | H | H | H | H | H | H | —C(S)NHCH$_3$ |
| 1-5 | H | H | H | H | H | H | —P(O)(OC$_2$H$_5$)$_2$ |
| 1-6 | H | H | H | H | H | H | —S(O)$_2$N(CH$_3$)$_2$ |
| 1-7 | H | H | H | H | H | H | —S(O)$_2$CH$_3$ |
| 1-8 | H | H | H | H | H | H | —P(S)(OCH$_3$)$_2$ |
| 1-9 | H | H | H | H | H | H | —P(O)[N(CH$_3$)$_2$]$_2$ |
| 1-10 | H | H | H | H | H | H | —CH$_2$C$_6$H$_5$ |
| 1-11 | H | H | H | H | H | H | —C(O)C$_2$H$_5$ |
| 1-12 | H | H | H | H | H | H | —C(O)OC$_2$H$_5$ |
| 1-13 | H | H | H | H | H | H | —C(O)OCH$_3$ |
| 1-14 | H | Cl | H | H | H | H | H |
| 1-15 | H | H | H | —CH$_3$ | H | H | H |
| 1-16 | H | —OCH$_3$ | H | H | H | H | H |
| 1-17 | H | —CH$_3$ | H | H | H | H | H |
| 1-18 | H | H | H | —OCH$_3$ | H | H | H |
| 1-19 | H | H | Cl | H | H | H | H |
| 1-20 | H | H | —OCH$_3$ | H | H | H | H |
| 1-21 | F | H | H | H | H | H | H |
| 1-22 | —OCH$_3$ | H | H | H | H | H | H |
| 1-23 | H | H | —CH$_3$ | H | H | H | H |
| 1-24 | H | H | H | H | H | H | —C(O)CH$_3$ |
| 1-25 | F | H | H | H | H | H | —P(O)[N(CH$_3$)$_2$]$_2$ |
| 1-26 | F | H | H | H | H | H | —P(S)(OC$_2$H$_5$)$_2$ |
| 1-27 | F | H | H | H | H | H | —C(S)NHCH$_3$ |
| 1-28 | F | H | H | H | H | H | —P(S)(OCH$_3$)$_2$ |
| 1-29 | H | H | H | H | H | H | H |
| 1-30* | H | H | H | H | H | H | H |
| 1-31** | H | H | H | H | H | H | H |
| 1-32 | —CH$_3$ | H | H | H | H | H | H |
| 1-33 | Cl | H | H | H | H | H | H |
| 1-34 | H | H | H | H | H | —CH$_3$ | H |
| 1-35 | H | H | H | H | —CH$_3$ | H | H |
| 1-36 | H | H | H | H | H | —C$_6$H$_5$ | H |
| 1-37 | H | H | H | H | H | H | —C(S)NH$_2$ |
| 1-38 | H | H | H | H | H | H | —C(S)NHC$_2$H$_3$ |
| 1-39 | H | H | H | H | H | H | —CHO |
| 1-40 | H | H | H | H | H | H | —CH$_2$OCH$_3$ |
| 1-41 | H | H | H | H | H | H | —C(S)NHCH(CH$_3$)$_2$ |
| 1-42 | H | H | H | H | H | H | —P(O)(OCH$_3$)$_2$ |
| 1-43 | —OCF$_3$ | H | H | H | H | H | —C(S)NH$_2$ |
| 1-44 | —OCF$_3$ | H | H | H | H | H | —C(S)NHC$_2$H$_5$ |
| 1-45 | —OCF$_3$ | H | H | H | H | H | —CHO |
| 1-46 | —OCF$_3$ | H | H | H | H | H | —CH$_2$OCH$_3$ |

TABLE 1-continued

Insecticidal Substituted Amino Heterocyclic Derivatives

| | | | | | | | |
|---|---|---|---|---|---|---|---|
| 1-47 | —OCF₃ | H | H | H | H | H | —P(S)(OC₂H₅)₂ |
| 1-48 | —OCF₃ | H | H | H | H | H | —C(O)NHCH₃ |
| 1-49 | —OCF₃ | H | H | H | H | H | —P(S)(OCH₃)₂ |
| 1-50 | —OCF₃ | H | H | H | H | H | —SO₂CH₃ |
| 1-51 | —OCF₃ | H | H | H | H | H | —P(O)[N(CH₃)₂]₂ |
| 1-52 | —OCF₃ | H | H | H | H | H | —C(O)OC₂H₅ |
| 1-53 | —OCF₃ | H | H | H | H | H | H |
| 1-54 | —OCF₃ | H | H | H | H | H | —C(S)NHCH₃ |
| 1-55 | —OCF₃ | H | H | H | H | H | —CN |
| 1-56 | —OCF₃ | H | F | H | H | H | —C(S)NH₂ |
| 1-57 | —OCF₃ | H | F | H | H | H | —C(S)NHCH₃ |
| 1-58 | —OCF₃ | H | F | H | H | H | —CN |
| 1-59 | —OCF₃ | H | F | H | H | H | —CHO |
| 1-60 | —OCF₃ | H | F | H | H | H | —P(S)(OC₂H₅)₂ |
| 1-61 | —OCF₃ | H | F | H | H | H | —P(S)(OCH₃)₂ |
| 1-62 | —OCF₃ | H | Cl | H | H | H | H |
| 1-63 | —OCF₃ | H | Cl | H | H | H | —C(S)NH₂ |
| 1-64 | —OCF₃ | H | Cl | H | H | H | —C(S)NHCH₃ |
| 1-65 | —OCF₃ | H | Cl | H | H | H | —CN |
| 1-66 | —OCF₃ | H | Cl | H | H | H | —CHO |
| 1-67 | —OCF₃ | H | Cl | H | H | H | —P(S)(OC₂H₅)₂ |
| 1-68 | —OCF₃ | H | Cl | H | H | H | —P(S)(OCH₃)₂ |
| 1-69 | —OCF₃ | H | Cl | H | H | H | —CH₂OCH₃ |
| 1-70 | —OCF₃ | H | Cl | H | H | H | —C(S)NHC₂H₅ |
| 1-71 | —OCF₃ | H | Cl | H | H | H | —C(S)NHCH(CH₃)₂ |
| 1-72 | —OCF₃ | H | Cl | H | H | H | —C(S)NHC₃H₇ |
| 1-73 | —OCF₃ | H | Cl | H | H | H | —C(O)C₂H₅ |
| 1-74 | —OCF₃ | H | Cl | H | H | H | —C(O)OC₂H₅ |
| 1-75 | —OCF₃ | H | Cl | H | H | H | —C(O)OCH₃ |
| 1-76 | —CF₃ | H | H | H | H | H | H |
| 1-77 | —CF₃ | H | H | H | H | H | —C(S)NH₂ |
| 1-78 | —CF₃ | H | H | H | H | H | —C(S)NHCH₃ |
| 1-79 | —CF₃ | H | H | H | H | H | —CN |
| 1-80 | —CF₃ | H | H | H | H | H | —CHO |
| 1-81 | —CF₃ | H | H | H | H | H | —P(S)(OC₂H₅)₂ |
| 1-82 | —CF₃ | H | H | H | H | H | —P(S)(OCH₃)₂ |
| 1-83 | —CF₃ | H | H | H | H | H | —CH₂OCH₃ |
| 1-84 | —CF₃ | H | H | H | H | H | —C(S)NHC₂H₅ |
| 1-85 | —CF₃ | H | H | H | H | H | —C(S)NHC₃H₇ |
| 1-86 | —CF₃ | H | H | H | H | H | —C(O)OC₂H₅ |
| 1-87 | —CF₃ | H | H | H | H | H | —SO₂CH₃ |
| 1-88 | —CF₃ | H | H | H | H | H | —SO₂CF₃ |
| 1-89 | —CF₃ | H | H | H | H | H | —C(O)CH₃ |
| 1-90 | —CF₃ | H | H | H | H | H | —CH₂C₆H₃ |
| 1-91 | —CF₃ | H | Cl | H | H | H | H |
| 1-92 | —CF₃ | H | Cl | H | H | H | —C(S)NH₂ |
| 1-93 | —CF₃ | H | Cl | H | H | H | —C(S)NHCH₃ |
| 1-94 | —CF₃ | H | Cl | H | H | H | —CN |
| 1-95 | —CF₃ | H | Cl | H | H | H | —CHO |
| 1-96 | —CF₃ | H | Cl | H | H | H | —P(S)(OC₂H₅)₂ |
| 1-97 | —CF₃ | H | Cl | H | H | H | —P(S)(OCH₃)₂ |
| 1-98 | —CF₃ | H | Cl | H | H | H | —C(O)OC₂H₅ |
| 1-99 | —CF₃ | H | Cl | H | H | H | —CH₂OCH₃ |
| 1-100 | —CF₃ | H | Cl | H | H | H | —CH₂C₆H₅ |
| 1-101 | —CF₃ | H | Cl | H | H | H | —SO₂CH₃ |
| 1-102 | Cl | H | Cl | H | H | H | H |
| 1-103 | Cl | H | Cl | H | H | H | —C(S)NH₂ |
| 1-104 | Cl | H | Cl | H | H | H | —C(S)NHCH₃ |
| 1-105 | Cl | H | Cl | H | H | H | —P(S)(OC₂H₅)₂ |
| 1-106 | Cl | H | Cl | H | H | H | —P(S)(OCH₃)₂ |
| 1-107 | Cl | H | Cl | H | H | H | —CN |
| 1-108 | Cl | H | Cl | H | H | H | —CHO |
| 1-109 | Cl | H | Cl | H | H | H | —CH₂OCH₃ |
| 1-110 | Cl | H | Cl | H | H | H | —CH₂C₆H₅ |
| 1-111 | —SF₅ | H | H | H | H | H | H |
| 1-112 | —SF₅ | H | H | H | H | H | —C(S)NH₂ |
| 1-113 | —SF₅ | H | H | H | H | H | —C(S)NHCH₃ |
| 1-114 | —SF₅ | H | H | H | H | H | —P(S)(OC₂H₅)₂ |
| 1-115 | —SF₅ | H | H | H | H | H | —P(S)(OCH₃)₂ |
| 1-116 | H | H | —SF₅ | H | H | H | H |
| 1-117 | H | H | —SF₅ | H | H | H | —C(S)NHCH₃ |
| 1-118 | H | —OCF₃ | H | H | H | H | H |
| 1-119 | H | —OCF₃ | H | H | H | H | —C(S)NH₂ |
| 1-120 | H | —OCF₃ | H | H | H | H | —C(S)NHCH₃ |
| 1-121 | H | —OCF₃ | H | H | H | H | —P(S)(OC₂H₅)₂ |
| 1-122 | H | H | —OCF₃ | H | H | H | H |
| 1-123 | H | H | —OCF₃ | H | H | H | —C(S)NH₂ |
| 1-124 | H | H | —OCF₃ | H | H | H | —C(S)NHCH₃ |

TABLE 1-continued

Insecticidal Substituted Amino Heterocyclic Derivatives

| | | | | | | | |
|---|---|---|---|---|---|---|---|
| 1-125 | H | H | —OCF$_3$ | H | H | H | —P(S)(OC$_2$H$_5$)$_2$ |
| 1-126 | H | H | H | —OCF$_3$ | H | H | H |
| 1-127 | H | H | H | —OCF$_3$ | H | H | —C(S)NH$_2$ |
| 1-128 | H | H | H | —OCF$_3$ | H | H | —C(S)NHCH$_3$ |
| 1-129 | H | H | H | —OCF$_3$ | H | H | —P(S)(OC$_2$H$_5$)$_2$ |
| 1-130 | Cl | H | —OCF$_3$ | H | H | H | H |
| 1-131 | Cl | H | —OCF$_3$ | H | H | H | —C(S)NH$_2$ |
| 1-132 | Cl | H | —OCF$_3$ | H | H | H | —C(S)NHCH$_3$ |
| 1-133 | Cl | H | —OCF$_3$ | H | H | H | —P(S)(OC$_2$H$_5$)$_2$ |
| 1-134 | H | —CF$_3$ | H | H | H | H | H |
| 1-135 | H | —CF$_3$ | H | H | H | H | —C(S)NH$_2$ |
| 1-136 | H | —CF$_3$ | H | H | H | H | —C(S)NHCH$_3$ |
| 1-137 | H | —CF$_3$ | H | H | H | H | —P(S)(OC$_2$H$_5$)$_2$ |
| 1-138 | H | H | —CF$_3$ | H | H | H | H |
| 1-139 | H | H | —CF$_3$ | H | H | H | —C(S)NH$_2$ |
| 1-140 | H | H | —CF$_3$ | H | H | H | —C(S)NHCH$_3$ |
| 1-141 | H | H | —CF$_3$ | H | H | H | —P(S)(OC$_2$H$_5$)$_2$ |
| 1-142 | H | H | H | —CF$_3$ | H | H | H |
| 1-143 | H | H | H | —CF$_3$ | H | H | —C(S)NH$_2$ |
| 1-144 | H | H | H | —CF$_3$ | H | H | —C(S)NHCH$_3$ |
| 1-145 | H | H | H | —CF$_3$ | H | H | —P(S)(OC$_2$H$_5$)$_2$ |
| 1-146 | —CN | H | H | H | H | H | H |
| 1-147 | —CN | H | H | H | H | H | —C(S)NH$_2$ |
| 1-148 | —CN | H | H | H | H | H | —C(S)NHCH$_3$ |
| 1-149 | —CN | H | H | H | H | H | —P(S)(OC$_2$H$_3$)$_2$ |
| 1-150 | H | H | Cl | H | H | H | H |
| 1-151 | H | H | Cl | H | H | H | —C(S)NH$_2$ |
| 1-152 | H | H | Cl | H | H | H | —C(S)NHCH$_3$ |
| 1-153 | H | H | Cl | H | H | H | —P(S)(OC$_2$H$_5$)$_2$ |
| 1-154 | H | F | H | H | H | H | H |
| 1-155 | H | F | H | H | H | H | —C(S)NH$_2$ |
| 1-156 | H | F | H | H | H | H | —C(S)NHCH$_3$ |
| 1-157 | H | F | H | H | H | H | —P(S)(OC$_2$H$_5$)$_2$ |
| 1-158 | Br | H | H | H | H | H | H |
| 1-159 | Br | H | H | H | H | H | —C(S)NH$_2$ |
| 1-160 | Br | H | H | H | H | H | —C(S)NHCH$_3$ |
| 1-161 | Br | H | H | H | H | H | —P(S)(OC$_2$H$_5$)$_2$ |
| 1-162 | H | Br | H | H | H | H | H |
| 1-163 | H | Br | H | H | H | H | —C(S)NH$_2$ |
| 1-164 | H | Br | H | H | H | H | —C(S)NHCH$_3$ |
| 1-165 | H | Br | H | H | H | H | —P(S)(OC$_2$H$_5$)$_2$ |
| 1-166 | H | H | Br | H | H | H | H |
| 1-167 | H | H | Br | H | H | H | —C(S)NH$_2$ |
| 1-168 | H | H | Br | H | H | H | —C(S)NHCH$_3$ |
| 1-169 | H | H | Br | H | H | H | —P(S)(OC$_2$H$_5$)$_2$ |
| 1-170 | H | H | H | Br | H | H | H |
| 1-171 | H | H | H | Br | H | H | —C(S)NH$_2$ |
| 1-172 | H | H | H | Br | H | H | —C(S)NHCH$_3$ |
| 1-173 | H | H | H | Br | H | H | —P(S)(OC$_2$H$_5$)$_2$ |
| 1-174 | —NO$_2$ | H | H | H | H | H | H |
| 1-175 | —NO$_2$ | H | H | H | H | H | —C(S)NH$_2$ |
| 1-176 | —NO$_2$ | H | H | H | H | H | —C(S)NHCH$_3$ |
| 1-177 | —NO$_2$ | H | H | H | H | H | —P(S)(OC$_2$H$_5$)$_2$ |
| 1-178 | —OCHF$_2$ | H | H | H | H | H | H |
| 1-179 | —OCHF$_2$ | H | H | H | H | H | —C(S)NH$_2$ |
| 1-180 | —OCHF$_2$ | H | H | H | H | H | —C(S)NHCH$_3$ |
| 1-181 | —OCHF$_2$ | H | H | H | H | H | —P(S)(OC$_2$H$_5$)$_2$ |
| 1-182 | F | H | F | H | H | H | H |
| 1-183 | F | H | F | H | H | H | —C(S)NH$_2$ |
| 1-184 | F | H | F | H | H | H | —C(S)NHCH$_3$ |
| 1-185 | F | H | F | H | H | H | —P(S)(OC$_2$H$_5$)$_2$ |
| 1-186 | Cl | H | F | H | H | H | H |
| 1-187 | Cl | H | F | H | H | H | —C(S)NH$_2$ |
| 1-188 | Cl | H | F | H | H | H | —C(S)NHCH$_3$ |
| 1-189 | Cl | H | F | H | H | H | —P(S)(OC$_2$H$_5$)$_2$ |
| 1-190 | F | H | Cl | H | H | H | H |
| 1-191 | F | H | Cl | H | H | H | —C(S)NH$_2$ |
| 1-192 | F | H | Cl | H | H | H | —C(S)NHCH$_3$ |
| 1-193 | F | H | Cl | H | H | H | —P(S)(OC$_2$H$_3$)$_2$ |
| 1-194 | Cl | H | H | H | —CH$_3$ | H | H |
| 1-195 | Cl | H | H | H | —CH$_3$ | H | —C(S)NH$_2$ |
| 1-196 | Cl | H | H | H | —CH$_3$ | H | —C(S)NHCH$_3$ |
| 1-197 | Cl | H | H | H | —CH$_3$ | H | —P(S)(OC$_2$H$_3$)$_2$ |
| 1-198 | Cl | H | H | H | H | —CH$_3$ | H |
| 1-199 | Cl | H | H | H | H | —CH$_3$ | —C(S)NH$_2$ |
| 1-200 | Cl | H | H | H | H | —CH$_3$ | —C(S)NHCH$_3$ |
| 1-201 | Cl | H | H | H | H | —CH$_3$ | —P(S)(OC$_2$H$_5$)$_2$ |
| 1-202 | Cl | H | H | H | H | —CF$_3$ | H |

TABLE 1-continued

Insecticidal Substituted Amino Heterocyclic Derivatives

| | | | | | | | |
|---|---|---|---|---|---|---|---|
| 1-203 | Cl | H | H | H | H | —CF₃ | —C(S)NH₂ |
| 1-204 | Cl | H | H | H | H | —CF₃ | —C(S)NHCH₃ |
| 1-205 | Cl | H | H | H | H | —CF₃ | —P(S)(OC₂H₅)₂ |
| 1-206 | —CF₃ | H | H | H | —CH₃ | H | H |
| 1-207 | —CF₃ | H | H | H | —CH₃ | H | —C(S)NH₂ |
| 1-208 | —CF₃ | H | H | H | —CH₃ | H | —C(S)NHCH₃ |
| 1-209 | —CF₃ | H | H | H | —CH₃ | H | —P(S)(OC₂H₅)₂ |
| 1-210 | —CF₃ | H | H | H | H | —CH₃ | H |
| 1-211 | —CF₃ | H | H | H | H | —CH₃ | —C(S)NH₂ |
| 1-212 | —CF₃ | H | H | H | H | —CH₃ | —C(S)NHCH₃ |
| 1-213 | —CF₃ | H | H | H | H | —CH₃ | —P(S)(OC₂H₅)₂ |
| 1-214 | Cl | H | —OCH₃ | H | H | H | H |
| 1-215 | Cl | H | —OCH₃ | H | H | H | —C(S)NH₂ |
| 1-216 | Cl | H | —OCH₃ | H | H | H | —C(S)NHCH₃ |
| 1-217 | Cl | H | —OCH₃ | H | H | H | —P(S)(OC₂H₅)₂ |
| 1-218 | —CF₃ | H | —OCH₃ | H | H | H | H |
| 1-219 | —CF₃ | H | —OCH₃ | H | H | H | —C(S)NH₂ |
| 1-220 | —CF₃ | H | —OCH₃ | H | H | H | —C(S)NHCH₃ |
| 1-220 | —CF₃ | H | —OCH₃ | H | H | H | —P(S)(OC₂H₅)₂ |
| 1-222 | Cl | H | —CH₃ | H | H | H | H |
| 1-223 | Cl | H | —CH₃ | H | H | H | —C(S)NH₂ |
| 1-224 | Cl | H | —CH₃ | H | H | H | —C(S)NHCH₃ |
| 1-225 | Cl | H | —CH₃ | H | H | H | —P(S)(OC₂H₅)₂ |
| 1-226 | Cl | H | —OCH₃ | H | H | H | H |
| 1-227 | Cl | H | —OCH₃ | H | H | H | —C(S)NH₂ |
| 1-228 | Cl | H | —OCH₃ | H | H | H | —C(S)NHCH₃ |
| 1-229 | Cl | H | —OCH₃ | H | H | H | —P(S)(OC₂H₅)₂ |
| 1-230 | F | H | H | H | H | H | —C(S)NHCO₂C₂H₅ |
| 1-231 | F | H | H | H | H | H | —C(S)NHCH₂CO₂C₂H₅ |
| 1-232 | F | H | H | H | H | H | —C(S)NHC(O)C₆H₅ |
| 1-233 | F | H | H | H | H | H | —C(S)NHC₃H₇ |
| 1-234 | F | H | H | H | H | H | —C(S)NHC₂H₅ |
| 1-235 | F | H | H | H | H | H | —C(S)NHC(CH₃)₃ |
| 1-236 | F | H | H | H | H | H | —C(S)NHC(O)CH₃ |
| 1-237 | F | H | H | H | H | H | —C(S)NHCH(CH₃)CH₂CO₂CH₃ |
| 1-238 | F | H | H | H | H | H | —C(S)NHCH(CH₃)CH₂CO₂C₂H₅ |
| 1-239 | F | H | H | H | H | H | —C(S)NH—⊲ |
| 1-240 | F | H | H | H | H | H | —C(S)NHCH₂CH(OCH₃)₂ |
| 1-241 | F | H | H | H | H | H | —C(S)NHC₂H₄CO₂CH₃ |
| 1-242 | F | H | H | H | H | H | —C(S)NHC₂H₄OCH₃ |
| 1-243 | F | H | H | H | H | H | —C(S)NHCH₂CO₂CH₃ |
| 1-244 | F | H | H | H | H | H | —C(S)NHCH(C₂H₅)CO₂CH₃ |
| 1-245 | F | H | H | H | H | H | —C(S)NHCH₂OCH₃ |
| 1-246 | F | H | F | H | H | H | H |
| 1-247 | F | H | F | H | H | H | —C(S)NHCH₃ |
| 1-248 | F | H | H | H | H | H | —C(NH)SH |
| 1-249 | F | H | H | H | —CH₃ | H | —C(S)NHCH₃ |
| 1-250 | F | H | Cl | H | H | H | —C(S)NHCH₃ |
| 1-251 | F | H | H | H | H | H | —CO₂C₂H₅ |
| 1-252 | F | H | H | H | H | H | —C(O)CH₃ |
| 1-253 | F | H | H | H | H | H | —S(O)₂N(CH₃)₂ |
| 1-254 | F | H | H | H | H | H | —C(O)CH(CH₃)₂ |
| 1-255 | F | H | H | H | H | H | —C(O)NHCH₃ |
| 1-256 | F | H | H | H | H | H | —P(O)(OC₂H₅)₂ |
| 1-257 | F | H | H | H | H | H | —C(S)NHCH(CH₃)CH₂OCH₅ |
| 1-258 | F | H | H | F | H | H | —C(S)NHC₃H₇ |
| 1-259 | F | H | H | F | H | H | —C(S)NHC₂H₄OCH₃ |
| 1-260* | H | H | H | H | H | H | —C(S)NH—CH₃ |
| 1-261** | H | H | H | H | H | H | —C(S)NH—CH₃ |
| 1-262 | H | H | H | H | H | H | —C(S)NH—CH₂—CF₃ |
| 1-263* | H | H | H | H | H | H | —C(S)NH—CH₂—CF₃ |
| 1-264** | H | H | H | H | H | H | —C(S)NH—CH₂—CF₃ |
| 1-265 | H | H | H | H | H | H | —C(S)NH—CH₂—COOCH₃ |
| 1-266* | H | H | H | H | H | H | —C(S)NH—CH₂—COOCH₃ |
| 1-267** | H | H | H | H | H | H | —C(S)NH—CH₂—COOCH₃ |
| 1-268 | H | H | H | H | H | H | —C(S)NH—CH₂—COOC₂H₅ |
| 1-269* | H | H | H | H | H | H | —C(S)NH—CH₂—COOC₂H₅ |
| 1-270** | H | H | H | H | H | H | —C(S)NH—CH₂—COOC₂H₃ |
| 1-271 | H | H | H | H | H | H | —C(S)NH—CH₂—CH₂—OCH₃ |
| 1-272* | H | H | H | H | H | H | —C(S)NH—CH₂—CH₂—OCH₃ |
| 1-273** | H | H | H | H | H | H | —C(S)NH—CH₂—CH₂—OCH₃ |
| 1-274 | F | H | H | H | H | H | C(S)NH—CH₂—CF₃ |
| 1-275 | H | Cl | H | H | H | H | C(S)NH—CH₃ |
| 1-276 | H | Cl | H | H | H | H | C(S)NH—COOCH₃ |

TABLE 1-continued

Insecticidal Substituted Amino Heterocyclic Derivatives

| | | | | | | | |
|---|---|---|---|---|---|---|---|
| 1-277 | H | Cl | H | H | H | H | C(S)NH—CH$_2$—CH$_2$—OCH$_3$ |
| 1-278 | H | Cl | t-Bu | H | H | H | H |
| 1-279 | H | Cl | t-Bu | H | H | H | C(S)—NH—CH$_3$ |
| 1-280 | H | Cl | t-Bu | H | H | H | C(S)—NH—CH$_2$—COOC$_2$H$_5$ |
| 1-281** | H | Cl | Me$^+$ | H | H | H | H |
| 1-282** | H | Cl | Me$^+$ | H | H | H | C(S)—NH—CH$_3$ |
| 1-283** | H | Cl | Me$^+$ | H | H | H | C(S)—NH—CH$_2$—COOCH$_3$ |
| 1-284** | H | Cl | Me$^+$ | H | H | H | C(S)—NH—CH$_2$—CH$_2$—OCH$_3$ |
| 1-285* | H | Cl | Me$^{++}$ | H | H | H | C(S)—NH—CH$_3$ |
| 1-286* | H | Cl | Me$^+$ | H | H | H | C(S)—NH—CH$_3$ |
| 1-287 | H | H | H | H | H | H |  |
| 1-288 | H | H | H | H | H | H |  |
| 1-289 | H | H | H | H | H | H | C(S)—NH—CH$_2$—CH(OCH$_3$)$_2$ |
| 1-290 | H | H | H | H | H | H | C(S)—NH—CH(CH$_3$)—CH$_2$CH$_2$CH$_3$ |
| 1-291 | H | H | H | H | H | H | C(S)—NH—CH(C$_2$H$_5$)$_2$ |
| 1-292 | H | H | H | H | H | H | C(S)—NH—CH(CH$_3$)—CH(CH$_3$)$_2$ |
| 1-293 | H | H | H | H | H | H |  |
| 1-294 | H | H | H | H | H | H | C(S)—NH—CH$_2$—CH(CH$_3$)$_2$ |
| 1-296 | H | H | H | H | H | H | C(S)—NH—CH$_2$—CH$_2$—CH$_3$ |
| 1-297 | H | H | H | H | H | H | C(S)—NH—CH$_2$—CH$_2$—CH$_2$—CH$_3$ |
| 1-298 | H | H | H | H | H | H | C(S)—NH—CH(CH$_3$)—CF$_3$ |
| 1-299 | H | H | H | H | H | H | C(S)—NH—CH$_2$CH$_2$OCH$_3$ |
| 1-300 | H | H | H | H | H | H | C(S)NH—CH$_2$CH$_2$COOCH$_3$ |
| 1-301 | H | H | H | H | H | H | C(S)NH—CH(CH$_3$)CH$_2$—COOC$_2$H$_5$ |
| 1-302 | H | H | H | H | H | H | C(S)—NH—CH$_2$CH$_2$CH$_2$—COOC$_2$H$_5$ |
| 1-303 | H | H | H | H | H | H | C(S)—NH—CH(CH(CH$_3$)$_2$)—COOCH$_3$ |
| 1-304 | H | H | H | H | H | H | C(S)—NH—CH(CH$_3$)COOC$_2$H$_5$ |
| 1-305 | H | H | H | H | H | H | C(S)—NH—CH(C$_2$H$_3$)COOCH$_3$ |
| 1-306 | H | H | H | H | H | H |  |
| 1-307 | H | H | H | H | H | H | C(S)—N(CH$_3$)$_2$ |
| 1-308* | H | H | H | H | H | H | C(S)—NH—CH$_2$—CH(OCH$_3$)$_2$ |
| 1-309* | H | H | H | H | H | H | C(S)—NH—CH(CH$_3$)CH$_2$CH$_2$CH$_3$ |
| 1-310* | H | H | H | H | H | H | C(S)—NH—CH(C$_2$H$_5$)$_2$ |
| 1-311* | H | H | H | H | H | H | C(S)—NH—CH(CH$_3$)CH(CH$_3$)$_2$ |
| 1-312* | H | H | H | H | H | H |  |
| 1-313* | H | H | H | H | H | H | C(S)—NH—C$_2$H$_5$ |
| 1-315* | H | H | H | H | H | H | C(S)—NH—CH$_2$CH$_3$ |
| 1-316* | H | H | H | H | H | H | C(S)—NH—CH$_2$CH$_2$CH$_2$CH$_3$ |
| 1-317* | H | H | H | H | H | H | C(S)—NH—CH(CH$_3$)—CF$_3$ |
| 1-318* | H | H | H | H | H | H | C(S)—NH—CH$_2$—CH(CH$_3$)$_2$ |
| 1-319* | H | H | H | H | H | H | C(S)—NH—CH$_2$CH$_2$—COOCH$_3$ |
| 1-320* | H | H | H | H | H | H | C(S)—NH—CH(CH$_3$)CH$_2$—COOC$_2$H$_5$ |
| 1-321* | H | H | H | H | H | H | C(S)—NH—(CH$_2$)$_3$—COOC$_2$H$_5$ |
| 1-322* | H | H | H | H | H | H | C(S)—NH CH(CH(CH$_3$)$_2$)—COOCH$_3$ |
| 1-323* | H | H | H | H | H | H | C(S)—NH—CH(CH$_3$)—COOC$_2$H$_5$ |
| 1-324* | H | H | H | H | H | H | C(S)—NH—CH(C$_2$H$_5$)COOCH$_3$ |

TABLE 1-continued

Insecticidal Substituted Amino Heterocyclic Derivatives

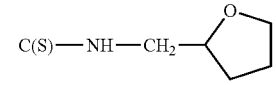

| | | | | | | | |
|---|---|---|---|---|---|---|---|
| 1-325* | H | H | H | H | H | H | C(S)—NH—CH$_2$-(tetrahydrofuran-2-yl) |
| 1-326* | H | H | H | H | H | H | C(S)NH—CH(CH$_3$)$_2$ |
| 1-327* | H | H | H | H | H | H | C(S)—NH-cyclopropyl |
| 1-328* | H | H | H | H | H | H | C(S)NH-cyclopentyl |
| 1-329* | H | H | H | H | H | H | C(S)—NH-(3-CF$_3$-cyclohexyl) |
| 1-330 | F | H | H | F | H | H | H |
| 1-331 | F | H | H | F | H | H | —C(S)NH$_2$ |
| 1-332 | F | H | H | F | H | H | —C(S)NHCH$_3$ |
| 1-333 | F | H | H | F | H | H | —P(S)(OC$_2$H$_5$)$_2$ |
| 1-334 | F | H | H | F | H | H | —C(S)NHC$_2$H$_5$ |
| 1-335 | F | H | H | F | H | H | —C(S)NHCH$_2$CF$_3$ |
| 1-336 | F | H | H | F | H | H | —C(S)NHCH(CH$_3$)CF$_3$ |
| 1-337 | F | H | H | F | H | H | —C(S)NHCH$_2$CH$_2$OCH$_3$ |
| 1-338 | F | H | H | F | H | H | —C(S)NHCH2COOCH$_3$ |
| 1-338 | F | H | H | F | H | H | —C(S)NHCH$_2$COOCH$_3$ |
| 1-339 | F | H | H | F | H | H | —C(S)NHCH(CH$_3$)$_2$ |
| 1-341 | F | H | H | F | H | H | —C(S)NH(CH$_2$)$_2$CH$_3$ |
| 1-342 | F | H | H | F | H | H | C(S)—NH-cyclopropyl |

Here and in the following tables:
*(1S)-amino isomer
**(1R)-amino isomer
+(2S) - Methylisomer
++(2R) - Methylisomer where A is —CHR$^5$—, B is —CHR$^8$—, Q is (D) and R$^{30}$ is hydrogen:

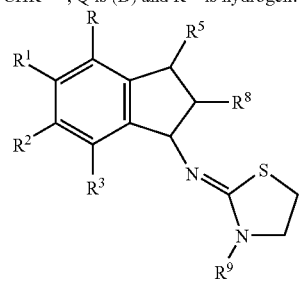

I-2

| Cmpd No. | R | R$^1$ | R$^2$ | R$^3$ | R$^5$ | R$^8$ | R$^9$ |
|---|---|---|---|---|---|---|---|
| 2-1 | Cl | H | H | H | H | H | 2-thiazoline-2-yl |
| 2-2 | H | H | H | H | H | H | —C(O)NHCH$_3$ |
| 2-3 | H | H | H | H | H | H | —P(O)[N(CH$_3$)$_2$]$_2$ |
| 2-4 | H | H | H | H | H | H | —P(O)(OC$_2$H$_5$)$_2$ |
| 2-5 | H | H | H | H | H | H | H |
| 2-6* | H | H | H | H | H | H | H |
| 2-7** | H | H | H | H | H | H | H |
| 2-8 | Cl | H | H | H | H | H | H |
| 2-9 | H | H | H | H | H | —CH$_2$C$_6$H$_5$ | H |
| 2-10 | Cl | H | H | H | H | H | —C(S)NH$_2$ |
| 2-11 | Cl | H | H | H | H | H | —C(S)NHCH$_3$ |

TABLE 1-continued

Insecticidal Substituted Amino Heterocyclic Derivatives

| Cmpd No. | R | R¹ | R² | R³ | R⁸ | | R⁹ |
|---|---|---|---|---|---|---|---|
| 2-12 | Cl | H | H | H | H | H | —P(S)(OC₂H₅)₂ |
| 2-13 | Cl | H | H | H | H | H | —CN |
| 2-14 | Cl | H | H | H | H | H | —CHO |
| 2-15 | Cl | H | H | H | H | H | —C(O)OC₂H₅ |
| 2-16 | Cl | H | H | H | H | H | —CH₂OCH₃ |
| 2-17 | Cl | H | H | H | H | H | —CH₂C₆H₅ |
| 2-18 | —CF₃ | H | H | H | H | H | H |
| 2-19 | —CF₃ | H | H | H | H | H | —C(S)NH₂ |
| 2-20 | —CF₃ | H | H | H | H | H | —C(S)NHCH₃ |
| 2-21 | —CF₃ | H | H | H | H | H | —P(S)(OC₂H₅)₂ |
| 2-22 | —OCF₃ | H | H | H | H | H | H |
| 2-23 | —OCF₃ | H | H | H | H | H | —C(S)NH₂ |
| 2-24 | —OCF₃ | H | H | H | H | H | —C(S)NHCH₃ |
| 2-25 | —OCF₃ | H | H | H | H | H | —P(S)(OC₂H₅)₂ |
| 2-26 | H | H | Cl | H | H | H | H |
| 2-27 | H | H | Cl | H | H | H | —C(S)NH₂ |
| 2-28 | H | H | Cl | H | H | H | —C(S)NHCH₃ |
| 2-29 | H | H | Cl | H | H | H | —P(S)(OC₂H₅)₂ |
| 2-30 | —CF₃ | H | Cl | H | H | H | H |
| 2-31 | —CF₃ | H | Cl | H | H | H | —C(S)NH₂ |
| 2-32 | —CF₃ | H | Cl | H | H | H | —C(S)NHCH₃ |
| 2-33 | —CF₃ | H | Cl | H | H | H | —P(S)(OC₂H₃)₂ |
| 2-34 | Cl | H | Cl | H | H | H | H |
| 2-35 | Cl | H | Cl | H | H | H | —C(S)NH₂ |
| 2-36 | Cl | H | Cl | H | H | H | —C(S)NHCH₃ |
| 2-37 | Cl | H | Cl | H | H | H | —P(S)(OC₂H₅)₂ |
| 2-38 | H | Cl | H | H | H | H | H |
| 2-39 | H | Cl | H | H | H | H | —C(S)NH₂ |
| 2-40 | H | Cl | H | H | H | H | —C(S)NHCH₃ |
| 2-41 | H | Cl | H | H | H | H | —P(S)(OC₂H₅)₂ |
| 2-42 | H | H | H | H | H | H | C(S)—NH—CH₂—COOCH₃ |
| 2-43 | H | H | H | H | H | H | C(S)—NH—CH₂—CH₂—OCH₃ |
| 2-44 | H | H | H | H | H | H | C(S)—NH—CH₃ |
| 2-45 | F | H | H | H | H | H | H |
| 2-46 | F | H | H | H | H | H | C(S)—NH—CH₃ |
| 2-47 | F | H | H | H | H | H | C(S)—NH—CH₂—CF₃ |
| 2-48 | F | H | H | H | H | H | C(S)—NH—CH₂—COOCH₃ |
| 2-49 | F | H | H | H | H | H | C(S)—NH—CH₂—COOC₂H₅ |
| 2-50 | F | H | H | H | H | H | C(S)—NH—CH₂—CH₂—OCH₃ |
| 2-51* | F | H | H | H | H | H | H |
| 2-52** | F | H | H | H | H | H | H |

*(1S)-amino isomer
**(1R)-amino isomer where A is —O—, B is —CHR⁸—, Q is (C) and R³⁰ is hydrogen:

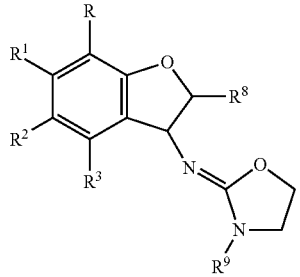

I-3

| Cmpd No. | R | R¹ | R² | R³ | R⁸ | R⁹ |
|---|---|---|---|---|---|---|
| 3-1 | H | H | H | H | H | H |
| 3-2 | Cl | H | H | H | H | H |
| 3-3 | Cl | H | H | H | H | —C(S)NH₂ |
| 3-4 | Cl | H | H | H | H | —C(S)NHCH₃ |
| 3-5 | Cl | H | H | H | H | —P(S)(OC₂H₅)₂ |
| 3-6 | —CF₃ | H | H | H | H | H |
| 3-7 | —CF₃ | H | H | H | H | C(S)NH₂ |
| 3-8 | —CF₃ | H | H | H | H | —C(S)NHCH₃ |
| 3-9 | —CF₃ | H | H | H | H | —P(S)(OC₂H₅)₂ |
| 3-10 | F | H | H | H | H | H |
| 3-11 | F | H | H | H | H | C(S)NH₂ |
| 3-12 | F | H | H | H | H | —C(S)NHCH₃ |
| 3-13 | F | H | H | H | H | —P(S)(OC₂H₅)₂ |

TABLE 1-continued

Insecticidal Substituted Amino Heterocyclic Derivatives

| Cmpd No. | | | | | | |
|---|---|---|---|---|---|---|
| 3-14 | —OCF$_3$ | H | H | H | H | H |
| 3-15 | —OCF$_3$ | H | H | H | H | C(S)NH$_2$ |
| 3-16 | —OCF$_3$ | H | H | H | H | —C(S)NHCH$_3$ |
| 3-17 | —OCF$_3$ | H | H | H | H | —P(S)(OC$_2$H$_5$)$_2$ |
| 3-18 | Cl | H | Cl | H | H | H |
| 3-19 | Cl | H | Cl | H | H | C(S)NH$_2$ |
| 3-20 | Cl | H | Cl | H | H | —C(S)NHCH$_3$ |
| 3-21 | Cl | H | Cl | H | H | —P(S)(OC$_2$H$_5$)$_2$ |
| 3-22 | H | H | Cl | H | H | H |
| 3-23 | H | H | Cl | H | H | C(S)NH$_2$ |
| 3-24 | H | H | Cl | H | H | —C(S)NHCH$_3$ |
| 3-25 | H | H | Cl | H | H | —P(S)(OC$_2$H$_5$)$_2$ |
| 3-26 | —CH$_3$ | H | H | H | H | H |
| 3-27 | —CH$_3$ | H | H | H | H | —C(S)NH$_2$ |
| 3-28 | —CH$_3$ | H | H | H | H | —C(S)NHCH$_3$ |
| 3-29 | —CH$_3$ | H | H | H | H | —P(S)(OC$_2$H$_5$)$_2$ |
| 3-30 | H | H | —CH$_3$ | H | H | H |
| 3-31 | H | H | —CH$_3$ | H | H | —C(S)NH$_2$ |
| 3-32 | H | H | —CH$_3$ | H | H | —C(S)NHCH$_3$ |
| 3-33 | H | H | —CH$_3$ | H | H | —P(S)(OC$_2$H$_5$)$_2$ | where A is —O—, B is —CHR$^8$—, Q is (D) and R$^{30}$ is hydrogen:

I-4

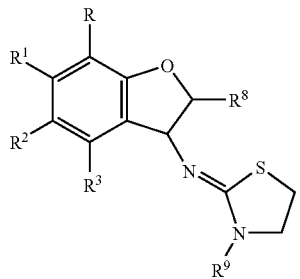

| Cmpd No. | R | R$^1$ | R$^2$ | R$^3$ | R$^8$ | R$^9$ |
|---|---|---|---|---|---|---|
| 4-1 | H | H | H | H | H | H |
| 4-2 | Cl | H | H | H | H | H |
| 4-3 | Cl | H | H | H | H | —C(S)NH$_2$ |
| 4-4 | Cl | H | H | H | H | —C(S)NHCH$_3$ |
| 4-5 | Cl | H | H | H | H | —P(S)(OC$_2$H$_5$)$_2$ |
| 4-6 | —CF$_3$ | H | H | H | H | H |
| 4-7 | —CF$_3$ | H | H | H | H | —C(S)NH$_2$ |
| 4-8 | —CF$_3$ | H | H | H | H | —C(S)NHCH$_3$ |
| 4-9 | —CF$_3$ | H | H | H | H | —P(S)(OC$_2$H$_5$)$_2$ |
| 4-10 | F | H | H | H | H | H |
| 4-11 | F | H | H | H | H | —C(S)NH$_2$ |
| 4-12 | F | H | H | H | H | —C(S)NHCH$_3$ |
| 4-13 | F | H | H | H | H | —P(S)(OC$_2$H$_5$)$_2$ |
| 4-14 | —OCF$_3$ | H | H | H | H | H |
| 4-15 | —OCF$_3$ | H | H | H | H | —C(S)NH$_2$ |
| 4-16 | —OCF$_3$ | H | H | H | H | —C(S)NHCH$_3$ |
| 4-17 | —OCF$_3$ | H | H | H | H | —P(S)(OC$_2$H$_5$)$_2$ |
| 4-18 | Cl | H | Cl | H | H | H |
| 4-19 | Cl | H | Cl | H | H | —C(S)NH$_2$ |
| 4-20 | Cl | H | Cl | H | H | —C(S)NHCH$_3$ |
| 4-21 | Cl | H | Cl | H | H | —P(S)(OC$_2$H$_5$)$_2$ |
| 4-22 | H | H | Cl | H | H | H |
| 4-23 | H | H | Cl | H | H | —C(S)NH$_2$ |
| 4-24 | H | H | Cl | H | H | —C(S)NHCH$_3$ |
| 4-25 | H | H | Cl | H | H | —P(S)(OC$_2$H$_5$)$_2$ |
| 4-26 | —CH$_3$ | H | H | H | H | H |
| 4-27 | —CH$_3$ | H | H | H | H | —C(S)NH$_2$ |
| 4-28 | —CH$_3$ | H | H | H | H | —C(S)NHCH$_3$ |
| 4-29 | —CH$_3$ | H | H | H | H | —P(S)(OC$_2$H$_5$)$_2$ |
| 4-30 | H | H | —CH$_3$ | H | H | H |
| 4-31 | H | H | —CH$_3$ | H | H | —C(S)NH$_2$ |
| 4-32 | H | H | —CH$_3$ | H | H | —C(S)NHCH$_3$ |
| 4-33 | H | H | —CH$_3$ | H | H | —P(S)(OC$_2$H$_5$)$_2$ | where A is —OCHR$^5$—, B is —CHR$^8$—, Q is (C) and R$^{30}$ is hydrogen:

TABLE 1-continued

Insecticidal Substituted Amino Heterocyclic Derivatives

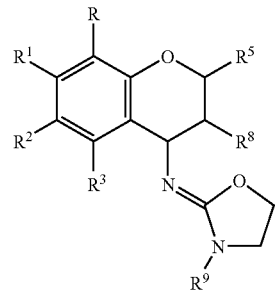

I-5

| Cmpd No. | R | R¹ | R² | R³ | R⁵ | R⁸ | R⁹ |
|---|---|---|---|---|---|---|---|
| 5-1 | H | H | H | H | H | H | H |
| 5-2 | H | —CH₃ | —OCH₃ | H | H | H | H |
| 5-3 | Cl | H | H | H | H | H | H |
| 5-4 | Cl | H | H | H | H | H | —C(S)NH₂ |
| 5-5 | Cl | H | H | H | H | H | —C(S)NHCH₃ |
| 5-6 | Cl | H | H | H | H | H | —P(S)(OC₂H₅)₂ |
| 5-7 | —CF₃ | H | H | H | H | H | H |
| 5-8 | —CF₃ | H | H | H | H | H | —C(S)NH₂ |
| 5-9 | —CF₃ | H | H | H | H | H | —C(S)NHCH₃ |
| 5-10 | —CF₃ | H | H | H | H | H | —P(S)(OC₂H₅)₂ |
| 5-11 | F | H | H | H | H | H | H |
| 5-12 | F | H | H | H | H | H | —C(S)NH₂ |
| 5-13 | F | H | H | H | H | H | —C(S)NHCH₃ |
| 5-14 | F | H | H | H | H | H | —P(S)(OC₂H₅)₂ |
| 5-15 | —OCF₃ | H | H | H | H | H | H |
| 5-16 | —OCF₃ | H | H | H | H | H | —C(S)NH₂ |
| 5-17 | —OCF₃ | H | H | H | H | H | —C(S)NHCH₃ |
| 5-18 | —OCF₃ | H | H | H | H | H | —P(S)(OC₂H₅)₂ |
| 5-19 | Cl | H | Cl | H | H | H | H |
| 5-20 | Cl | H | Cl | H | H | H | —C(S)NH₂ |
| 5-21 | Cl | H | Cl | H | H | H | —C(S)NHCH₃ |
| 5-22 | Cl | H | Cl | H | H | H | —P(S)(OC₂H₅)₂ |
| 5-23 | H | H | Cl | H | H | H | H |
| 5-24 | H | H | Cl | H | H | H | —C(S)NH₂ |
| 5-25 | H | H | Cl | H | H | H | —C(S)NHCH₃ |
| 5-26 | H | H | Cl | H | H | H | —P(S)(OC₂H₅)₂ |
| 5-27 | —CH₃ | H | H | H | H | H | H |
| 5-28 | —CH₃ | H | H | H | H | H | —C(S)NH₂ |
| 5-29 | —CH₃ | H | H | H | H | H | —C(S)NHCH₃ |
| 5-30 | —CH₃ | H | H | H | H | H | —P(S)(OC₂H₅)₂ |
| 5-31 | H | H | —CH₃ | H | H | H | H |
| 5-32 | H | H | —CH₃ | H | H | H | —C(S)NH₂ |
| 5-33 | H | H | —CH₃ | H | H | H | —C(S)NHCH₃ |
| 5-34 | H | H | —CH₃ | H | H | H | —P(S)(OC₂H₅)₂ | where A is —CHR⁵CHR⁶—, B is —CHR⁸—, Q is (D) and R³⁰ is hydrogen:

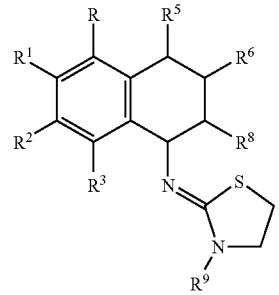

I-6

| Cmpd No. | R | R¹ | R² | R³ | R⁵ | R⁶ | R⁸ | R⁹ |
|---|---|---|---|---|---|---|---|---|
| 6-1 | H | H | H | H | H | H | H | H |
| 6-2 | Cl | H | H | H | H | H | H | H |
| 6-3 | Cl | H | H | H | H | H | H | —C(S)NH₂ |
| 6-4 | Cl | H | H | H | H | H | H | —C(S)NHCH₃ |
| 6-5 | Cl | H | H | H | H | H | H | —P(S)(OC₂H₅)₂ |
| 6-6 | —CF₃ | H | H | H | H | H | H | H |
| 6-7 | —CF₃ | H | H | H | H | H | H | —C(S)NH₂ |
| 6-8 | —CF₃ | H | H | H | H | H | H | —C(S)NHCH₃ |

TABLE 1-continued

Insecticidal Substituted Amino Heterocyclic Derivatives

| Cmpd No. | | | | | | | | |
|---|---|---|---|---|---|---|---|---|
| 6-9 | —CF$_3$ | H | H | H | H | H | H | —P(S)(OC$_2$H$_5$)$_2$ |
| 6-10 | F | H | H | H | H | H | H | H |
| 6-11 | F | H | H | H | H | H | H | —C(S)NH$_2$ |
| 6-12 | F | H | H | H | H | H | H | —C(S)NHCH$_3$ |
| 6-13 | F | H | H | H | H | H | H | —P(S)(OC$_2$H$_5$)$_2$ |
| 6-14 | —OCF$_3$ | H | H | H | H | H | H | H |
| 6-15 | —OCF$_3$ | H | H | H | H | H | H | —C(S)NH$_2$ |
| 6-16 | —OCF$_3$ | H | H | H | H | H | H | —C(S)NHCH$_3$ |
| 6-17 | —OCF$_3$ | H | H | H | H | H | H | —P(S)(OC$_2$H$_5$)$_2$ |
| 6-18 | Cl | H | Cl | H | H | H | H | H |
| 6-19 | Cl | H | Cl | H | H | H | H | —C(S)NH$_2$ |
| 6-20 | Cl | H | Cl | H | H | H | H | —C(S)NHCH$_3$ |
| 6-21 | Cl | H | Cl | H | H | H | H | —P(S)(OC$_2$H$_5$)$_2$ |
| 6-22 | H | H | Cl | H | H | H | H | H |
| 6-23 | H | H | Cl | H | H | H | H | —C(S)NH$_2$ |
| 6-24 | H | H | Cl | H | H | H | H | —C(S)NHCH$_3$ |
| 6-25 | H | H | Cl | H | H | H | H | —P(S)(OC$_2$H$_5$)$_2$ |
| 6-26 | —CH$_3$ | H | H | H | H | H | H | H |
| 6-27 | —CH$_3$ | H | H | H | H | H | H | —C(S)NH$_2$ |
| 6-28 | —CH$_3$ | H | H | H | H | H | H | —C(S)NHCH$_3$ |
| 6-29 | —CH$_3$ | H | H | H | H | H | H | —P(S)(OC$_2$H$_5$)$_2$ |
| 6-30 | H | H | —CH$_3$ | H | H | H | H | H |
| 6-31 | H | H | —CH$_3$ | H | H | H | H | —C(S)NH$_2$ |
| 6-32 | H | H | —CH$_3$ | H | H | H | H | —C(S)NHCH$_3$ |
| 6-33 | H | H | —CH$_3$ | H | H | H | H | —P(S)(OC$_2$H$_5$)$_2$ |
| 6-34 | H | H | H | H | H | H | H | C(S)—NH—CH$_2$—CF$_3$ |
| 6-35 | H | H | H | H | H | H | H | C(S)—NH—CH$_2$—CH$_2$—OCH$_3$ |
| 6-36 | H | H | H | H | H | H | H | C(S)—NH—CH$_2$—COOCH$_3$ |
| 6-37 | H | H | H | H | H | H | H | C(S)—NH—CH$_2$—COOC$_2$H$_5$ |
| 6-38 | H | H | H | H | H | H | H | H |
| 6-39 | H | H | H | H | H | H | H | H |
| 6-40 | F | H | H | H | H | H | H | H |
| 6-41 | F | H | H | H | H | H | H | C(S)—NH—CH$_3$ |
| 6-42 | F | H | H | H | H | H | H | C(S)—NH—CH$_2$—CF$_3$ |
| 6-43 | F | H | H | H | H | H | H | C(S)—NH—CH$_2$—CH$_2$—OCH$_3$ |
| 6-44 | F | H | H | H | H | H | H | C(S)—NH—CH$_2$—COOCH$_3$ |
| 6-45 | F | H | H | H | H | H | H | P(O)(N(CH$_3$)$_2$)$_2$ | where A is —CHR$^5$CHR$^6$—, B is —CHR$^8$—, Q is (C) and R$^{30}$ is hydrogen:

I-7

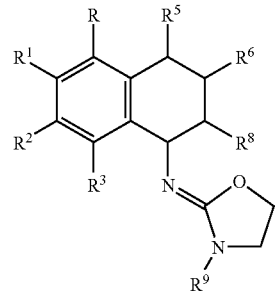

| Cmpd No. | R | R$^1$ | R$^2$ | R$^3$ | R$^5$ | R$^6$ | R$^8$ | R$^9$ |
|---|---|---|---|---|---|---|---|---|
| 7-1 | H | H | H | H | H | H | H | H |
| 7-2 | Cl | H | H | H | H | H | H | H |
| 7-3 | Cl | H | H | H | H | H | H | —C(S)NH$_2$ |
| 7-4 | Cl | H | H | H | H | H | H | —C(S)NHCH$_3$ |
| 7-5 | Cl | H | H | H | H | H | H | —P(S)(OC$_2$H$_5$)$_2$ |
| 7-6 | —CF$_3$ | H | H | H | H | H | H | H |
| 7-7 | —CF$_3$ | H | H | H | H | H | H | —C(S)NH$_2$ |
| 7-8 | —CF$_3$ | H | H | H | H | H | H | —C(S)NHCH$_3$ |
| 7-9 | —CF$_3$ | H | H | H | H | H | H | —P(S)(OC$_2$H$_5$)$_2$ |
| 7-10 | F | H | H | H | H | H | H | H |
| 7-11 | F | H | H | H | H | H | H | —C(S)NH$_2$ |
| 7-12 | F | H | H | H | H | H | H | —C(S)NHCH$_3$ |
| 7-13 | F | H | H | H | H | H | H | —P(S)(OC$_2$H$_5$)$_2$ |
| 7-14 | —OCF$_3$ | H | H | H | H | H | H | H |
| 7-15 | —OCF$_3$ | H | H | H | H | H | H | —C(S)NH$_2$ |
| 7-16 | —OCF$_3$ | H | H | H | H | H | H | —C(S)NHCH$_3$ |
| 7-17 | —OCF$_3$ | H | H | H | H | H | H | —P(S)(OC$_2$H$_5$)$_2$ |
| 7-18 | Cl | H | Cl | H | H | H | H | H |
| 7-19 | Cl | H | Cl | H | H | H | H | —C(S)NH$_2$ |
| 7-20 | Cl | H | Cl | H | H | H | H | —C(S)NHCH$_3$ |
| 7-21 | Cl | H | Cl | H | H | H | H | —P(S)(OC$_2$H$_5$)$_2$ |
| 7-22 | H | H | Cl | H | H | H | H | H |

TABLE 1-continued

Insecticidal Substituted Amino Heterocyclic Derivatives

| | | | | | | | | |
|---|---|---|---|---|---|---|---|---|
| 7-23 | H | H | Cl | H | H | H | H | —C(S)NH$_2$ |
| 7-24 | H | H | Cl | H | H | H | H | —C(S)NHCH$_3$ |
| 7-25 | H | H | Cl | H | H | H | H | —P(S)(OC$_2$H$_5$)$_2$ |
| 7-26 | —CH$_3$ | H | H | H | H | H | H | H |
| 7-27 | —CH$_3$ | H | H | H | H | H | H | —C(S)NH$_2$ |
| 7-28 | —CH$_3$ | H | H | H | H | H | H | —C(S)NHCH$_3$ |
| 7-29 | —CH$_5$ | H | H | H | H | H | H | —P(S)(OC$_2$H$_5$)$_2$ |
| 7-30 | H | H | —CH$_3$ | H | H | H | H | H |
| 7-31 | H | H | —CH$_3$ | H | H | H | H | —C(S)NH$_2$ |
| 7-32 | H | H | —CH$_3$ | H | H | H | H | —C(S)NHCH$_3$ |
| 7-33 | H | H | —CH$_3$ | H | H | H | H | —P(S)(OC$_2$H$_5$)$_2$ |
| 7-34 | H | H | H | H | H | H | H | H |
| 7-35** | H | H | H | H | H | H | H | H |
| 7-36 | H | H | H | H | H | H | H | C(S)—NH—CH$_3$ |
| 7-37 | H | H | H | H | H | H | H | C(S)—NH—CH$_2$—CF$_3$ |
| 7-38 | H | H | H | H | H | H | H | C(S)—NH—CH$_2$—CH$_2$—OCH$_3$ |
| 7-39 | H | H | H | H | H | H | H | C(S)—NH—CH$_2$—COOC$_2$H$_5$ |
| 7-40 | H | H | H | H | H | H | H | —CH$_2$—C$_6$H$_5$ |
| 7-41 | F | H | H | H | H | H | H | C(S)—NH—CH$_2$—CF$_3$ |
| 7-42 | F | H | H | H | H | H | H | C(S)—NH—CH$_2$—CH$_3$ |
| 7-43 | F | H | H | H | H | H | H | C(S)—NH—CH$_2$—CH$_2$—OCH$_3$ |
| 7-44 | F | H | H | H | H | H | H | C(S)—NH—CH$_2$—COOCH$_3$ |
| 7-45 | F | H | H | H | H | H | H | C(S)—NH—CH(CH$_3$)—COOC$_2$H$_5$ |
| 7-46* | H | H | H | H | H | H | H | C(S)—NH—CH$_3$ |
| 7-47* | H | H | H | H | H | H | H | C(S)—NH—CH$_2$—CH$_2$—OCH$_3$ |
| 7-48* | H | H | H | H | H | H | H | C(S)—NH—CH$_2$—CF$_3$ |
| 7-49* | H | H | H | H | H | H | H | C(S)—NH—CH$_2$—COOC$_2$H$_5$ |
| 7-50* | H | H | H | H | H | H | H | C(S)—NH—CH$_2$CH(OCH$_3$)$_2$ |
| 7-51* | H | H | H | H | H | H | H | C(S)—NH—CH(CH$_3$) CH$_2$CH$_2$—CH$_3$ |
| 7-52* | H | H | H | H | H | H | H | C(S)—NH—CH(C$_2$H$_5$)$_2$ |
| 7-53* | H | H | H | H | H | H | H | C(S)—NH—CH(CH$_3$)CH(CH$_3$)$_2$ |
| 7-54* | H | H | H | H | H | H | H | C(S)—NH—CH$_2$—cyclopropyl |
| 7-55* | H | H | H | H | H | H | H | C(S)—NH—C$_2$H$_5$ |
| 7-57* | H | H | H | H | H | H | H | C(S)—NH—CH$_2$CH$_2$CH$_3$ |
| 7-58* | H | H | H | H | H | H | H | C(S)—NH—(CH$_2$)$_3$CH$_3$ |
| 7-59* | H | H | H | H | H | H | H | C(S)—NH—CH(CH$_3$)—CF$_3$ |
| 7-60* | H | H | H | H | H | H | H | C(S)—NH—CH$_2$—CH(CH$_3$)$_2$ |
| 7-61* | H | H | H | H | H | H | H | C(S)—NH—(CH$_2$)$_2$COOCH$_3$ |
| 7-62* | H | H | H | H | H | H | H | C(S)—NH—CH(CH$_3$) CH$_2$—COOC$_2$H$_5$ |
| 7-63* | H | H | H | H | H | H | H | C(S)—NH—(CH$_2$)$_3$—COOC$_2$H$_5$ |
| 7-64* | H | H | H | H | H | H | H | C(S)—NH—CH(CH(CH$_3$)$_2$)—COOCH$_3$ |
| 7-65* | H | H | H | H | H | H | H | C(S)—NH—CH(CH$_3$)COOC$_2$H$_5$ |
| 7-66* | H | H | H | H | H | H | H | C(S)—NH—CH(C$_2$H$_5$)COOCH$_3$ |
| 7-67* | H | H | H | H | H | H | H | C(S)—NH—CH$_2$-(tetrahydrofuran-2-yl) |
| 7-68* | H | H | H | H | H | H | H | C(S)NHCH(CH$_3$)$_2$ |
| 7-69* | H | H | H | H | H | H | H | C(S)—NH-cyclopropyl |
| 7-70* | H | H | H | H | H | H | H | C(S)NH-cyclopentyl |
| 7-71* | H | H | H | H | H | H | H | C(S)NH—C(CH$_3$)(CH$_2$—CH$_2$Cl)$_2$ |
| 7-72 | H | H | H | H | H | H | H | C(S)NH—CH$_2$CH(OCH$_3$)$_2$ |
| 7-73 | H | H | H | H | H | H | H | C(S)NH—CH(CH$_3$)CH$_2$—CH$_2$CH$_3$ |
| 7-74 | H | H | H | H | H | H | H | C(S)NH—CH(C$_2$H$_5$)$_2$ |
| 7-75 | H | H | H | H | H | H | H | C(S)NH—CH(CH$_3$)—CH(CH$_3$)$_2$ |
| 7-76 | H | H | H | H | H | H | H | C(S)—NH—CH$_2$-cyclopropyl |
| 7-78 | H | H | H | H | H | H | H | C(S)NH—(CH$_2$)$_3$CH$_3$ |
| 7-79 | H | H | H | H | H | H | H | C(S)NH—CH(CH$_3$)—CF$_3$ |
| 7-80 | H | H | H | H | H | H | H | C(S)NH—CH$_2$CH(CH$_3$)$_2$ |
| 7-81 | H | H | H | H | H | H | H | C(S)NH—CH$_2$CH$_2$—COOCH$_3$ |
| 7-82 | H | H | H | H | H | H | H | C(S)NH—CH$_2$COOC$_2$H$_5$ |
| 7-83 | H | H | H | H | H | H | H | C(S)NH—(CH$_2$)$_3$COOC$_2$H$_5$ |
| 7-84 | H | H | H | H | H | H | H | C(S)NH—CH(CH(CH$_3$)$_2$)—COOCH$_3$ |

TABLE 1-continued

Insecticidal Substituted Amino Heterocyclic Derivatives

| 7-85 | H | H | H | H | H | H | H | C(S)NH—CH(CH$_3$)COOC$_2$H$_5$ |
| 7-86 | H | H | H | H | H | H | H | C(S)NH—CH(C$_2$H$_5$)COOCH$_3$ |
| 7-87 | H | H | H | H | H | H | H | 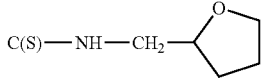 |
| 7-88 | H | H | H | H | H | H | H | C(S)NH—CH(CH$_3$)$_2$ |
| 7-89 | H | H | H | H | H | H | H | 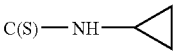 |
| 7-90 | H | H | H | H | H | H | H | 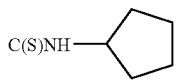 |
| 7-91 | H | H | H | H | H | H | H | 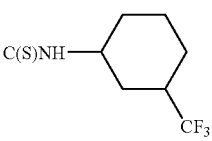 | where A is S—CHR$^5$—, B is —CHR$^8$—, Q is C and R$^{30}$ is hydrogen

I-8

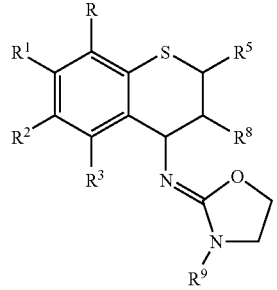

| Cmpd No. | R | R$^1$ | R$^2$ | R$^3$ | R$^5$ | R$^8$ | R$^9$ |
|---|---|---|---|---|---|---|---|
| 8-1 | H | H | H | H | H | H | C(S)—NH—CH$_3$ |
| 8-2 | H | H | H | H | H | H | P(S)(OC$_2$H$_5$)$_2$ |
| 8-3 | H | H | H | H | H | H | C(S)NH$_2$ |
| 8-4 | F | H | H | H | H | H | H |
| 8-5 | F | H | H | H | H | H | C(S)—NH—CH$_3$ |
| 8-6 | F | H | H | H | H | H | C(S)—NH—CH$_2$—COOC$_2$H$_5$ |
| 8-7 | F | H | H | H | H | H | C(S)—NH—CH$_2$—CH$_2$—OCH$_3$ |
| 8-8 | F | H | H | H | H | H | P(S)(OC$_2$H$_5$)$_2$ |
| 8-9 | F | H | H | H | H | H | C(S)—NH—CH$_2$—CF$_3$ |
| 8-10 | H | H | Cl | H | H | H | C(S)—NH—CH$_3$ |
| 8-11 | H | H | Cl | H | H | H | C(S)—NH—CH$_2$CF$_3$ |
| 8-12 | Cl | H | Cl | H | H | H | C(S)—NH—CH$_3$ |
| 8-13 | H | H | CH$_3$ | H | H | H | C(S)—NH—CH$_3$ | where A is —CHR$^5$—, B is —CHR$^8$, Q is (E), R$^{30}$ is H

I-9

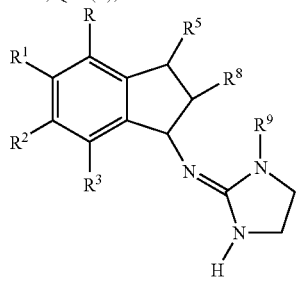

| Cmpd No. | R | R$^1$ | R$^2$ | R$^3$ | R$^5$ | R$^8$ | R$^9$ |
|---|---|---|---|---|---|---|---|
| 9-1 | H | H | H | H | H | H | C(S)—NH—CH$_3$ |

The following table sets forth some additional examples of substituted ethyl carboxamide and thiocarboxamide intermediates of formula IA:

TABLE 1A

Substituted Ethyl Carboxamide and Thiocarboxamide Intermediates

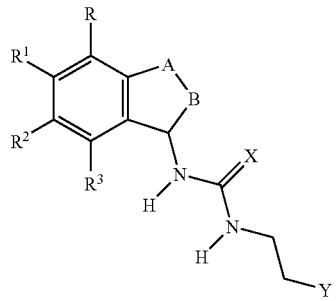

IA

| Cmpd. No. | R | $R^1$ | $R^2$ | $R^3$ | A | B | X | Y |
|---|---|---|---|---|---|---|---|---|
| IA-1 | Cl | H | H | H | —$CH_2$— | —$CH_2$— | O | Cl |
| IA-2 | H | H | H | H | —$CH_2$— | —$CH_2$— | O | Cl |
| IA-3 | —$CH_3$ | H | H | H | —$CH_2$— | —$CH_2$— | O | Cl |
| IA-4 | H | H | H | —$CH_3$ | —$CH_2$— | —$CH_2$— | O | Cl |
| IA-5 | H | H | —$CH_3$ | H | —$CH_2$— | —$CH_2$— | O | Cl |
| IA-6 | H | H | Cl | H | —$CH_2$— | —$CH_2$— | O | Cl |
| IA-7 | H | H | H | —$OCH_3$ | —$CH_2$— | —$CH_2$— | O | Cl |
| IA-8 | —$OCH_3$ | H | H | H | —$CH_2$— | —$CH_2$— | O | Cl |
| IA-9 | F | H | H | H | —$CH_2$— | —$CH_2$— | O | Cl |
| IA-10 | H | H | H | H | —$CH_2$— | —$CH(CH_3)$— | O | Cl |
| IA-11 | H | H | H | H | —$CH(CH_3)$— | —$CH_2$— | O | Cl |
| IA-12 | H | H | H | H | —$CH(C_2H_5)$— | —$CH_2$— | O | Cl |
| IA-13 | F | H | F | H | —$CH_2$— | —$CH_2$— | O | Cl |
| IA-14 | F | H | H | H | —$CH(CH_3)$— | —$CH_2$— | O | Cl |
| IA-15 | F | H | Cl | H | —$CH_2$— | —$CH_2$— | O | Cl |
| IA-16 | F | Cl | H | H | —$CH_2$— | —$CH_2$— | O | Cl |
| IA-17 | H | H | H | H | —$CH_2$— | —$CH_2$— | S | Cl |
| IA-18 | H | H | H | H | —$C_2H_4$— | —$CH_2$— | S | Cl |
| IA-19 | H | H | H | H | —O— | —$CH_2$— | S | Cl |
| IA-20 | F | H | H | H | —S—$CH_2$ | —$CH_2$— | O | Cl |
| IA-21 | F | H | H | F | —$CH_2$— | —$CH_2$— | O | Cl |
| I-A22* | H | H | H | H | —$CH_2$— | —$CH_2$— | O | Cl |
| IA-23* | F | H | H | H | —$CH_2$— | —$CH_2$— | O | Cl |
| IA-24 | H | H | H | H | —$C_2H_4$— | —$CH_2$— | O | Cl |
| IA-25* | H | H | H | H | —$C_2H_4$— | —$CH_2$— | O | Cl |

The following table sets forth physical characterizing data for certain compounds of formula I of the present invention:

TABLE 2

Insecticidal Substituted Amino Heterocyclic and Heteroaryl Derivatives Compound Characterization

| | Molecular Formula | Melting Point (° C.) of Solids Or Physical State or log P (HCOOH) [1)] |
|---|---|---|
| 1-1 | $C_{13}H_{13}N_3O$ | 101-102° C. |
| 1-2 | $C_{16}H_{23}N_2O_3PS$ | OIL |
| 1-3 | $C_{14}H_{17}N_3O_2$ | SOLID |
| 1-4 | $C_{14}H_{17}N_3OS$ | SOLID |
| 1-5 | $C_{16}H_{23}N_2O_4P$ | OIL |
| 1-6 | $C_{14}H_{19}N_3O_3S$ | OIL |
| 1-7 | $C_{13}H_{16}N_2O_3S$ | OIL |
| 1-8 | $C_{14}H_{19}N_2O_3PS$ | OIL |
| 1-9 | $C_{16}H_{25}N_4O_2P$ | OIL |
| 1-10 | $C_{19}H_{20}N_2O$ | OIL |
| 1-11 | $C_{15}H_{18}N_2O_2$ | SOLID |
| 1-12 | $C_{15}H_{18}N_2O_3$ | 85-87° C. |
| 1-13 | $C_{14}H_{16}N_2O_3$ | 119-120° C. |
| 1-14 | $C_{12}H_{13}ClN_2O$ | 117-120° C. |
| 1-15 | $C_{13}H_{16}N_2O$ | 112-113° C. |
| 1-16 | $C_{13}H_{16}N_2O_2$ | 99-101° C. |
| 1-17 | $C_{13}H_{16}N_2O$ | 135-137° C. |
| 1-18 | $C_{13}H_{16}N_2O_2$ | 118-119° C. |
| 1-19 | $C_{12}H_{13}ClN_2O$ | 95-96° C. |
| 1-20 | $C_{13}H_{16}N_2O_2$ | LIQUID |
| 1-21 | $C_{12}H_{13}FN_2O$ | 93-94° C. |
| 1-22 | $C_{13}H_{16}N_2O_2$ | SOLID |
| 1-23 | $C_{13}H_{16}N_2O$ | SOLID |
| 1-24 | $C_{14}H_{16}N_2O_2$ | 87-88° C. |
| 1-25 | $C_{16}H_{24}FN_4O_2P$ | OIL |
| 1-26 | $C_{16}H_{22}FN_2O_3PS$ | OIL |
| 1-27 | $C_{14}H_{16}FN_3OS$ | 146-147° C. |
| 1-28 | $C_{14}H_{18}FN_2O_3PS$ | OIL |
| 1-29 | $C_{12}H_{14}N_2O$ | 88-90° C. |
| 1-30 | $C_{12}H_{14}N_2O$ | OIL |
| 1-31 | $C_{12}H_{14}N_2O$ | OIL |
| 1-32 | $C_{13}H_{16}N_2O$ | 65-66° C. |

TABLE 2-continued

Insecticidal Substituted Amino Heterocyclic and
Heteroaryl Derivatives Compound Characterization

| | Molecular Formula | Melting Point (° C.) of Solids Or Physical State or log P (HCOOH) [1] |
|---|---|---|
| 1-33 | $C_{12}H_{13}ClN_2O$ | 72-74° C. |
| 1-34 | $C_{13}H_{16}N_2O$ | SOLID |
| 1-35 | $C_{13}H_{16}N_2O$ | 108-112° C. |
| 1-36 | $C_{18}H_{18}N_2O$ | 145-150° C. |
| 1-230 | $C_{16}H_{18}FN_3O_3S$ | 124-125° C. |
| 1-231 | $C_{17}H_{20}FN_3O_3S$ | 108-109° C. |
| 1-232 | $C_{20}H_{18}FN_3O_2S$ | 120-121° C. |
| 1-233 | $C_{16}H_{20}FN_3OS$ | 123-124° C. |
| 1-234 | $C_{15}H_{18}FN_3OS$ | 123-124° C. |
| 1-235 | $C_{17}H_{22}FN_3OS$ | 101-102° C. |
| 1-237 | $C_{17}H_{22}FN_3O_2S$ | OIL |
| 1-238 | $C_{19}H_{24}FN_3O_3S$ | OIL |
| 1-239 | $C_{16}H_{18}FN_3OS$ | 149-150° C. |
| 1-240 | $C_{17}H_{22}FN_3O_3S$ | OIL |
| 1-241 | $C_{17}H_{20}FN_3O_3S$ | 84-85° C. |
| 1-242 | $C_{16}H_{20}FN_3O_2S$ | 84-85° C. |
| 1-243 | $C_{16}H_{18}FN_3O_3S$ | 120-121° C. |
| 1-244 | $C_{18}H_{22}FN_3O_3S$ | OIL |
| 1-245 | $C_{15}H_{18}FN_3O_2S$ | 105-106° C. |
| 1-246 | $C_{12}H_{12}F_2N_2O$ | 84-86° C. |
| 1-247 | $C_{14}H_{15}F_2N_3OS$ | 122-123° C. |
| 1-248 | $C_{13}H_{14}FN_3OS$ | 152-153° C. |
| 1-249 | $C_{15}H_{18}FN_3OS$ | 148-152° C. |
| 1-250 | $C_{14}H_{15}ClFN_3OS$ | 124-126° C. |
| 1-251 | $C_{15}H_{17}FN_2O_3$ | 112-113° C. |
| 1-252 | $C_{14}H_{15}FN_2O_2$ | OIL |
| 1-253 | $C_{14}H_{18}FN_3O_3$ | 98-100° C. |
| 1-254 | $C_{16}H_{19}FN_2O_2$ | OIL |
| 1-255 | $C_{14}H_{16}FN_3O_2$ | 128-129° C. |
| 1-256 | $C_{16}H_{22}FN_2O_4P$ | OIL |
| 1-257 | $C_{15}H_{16}FN_3O_2S$ | OIL |
| 1-258 | $C_{16}H_{19}F_2N_3OS$ | OIL |
| 1-259 | $C_{16}H_{19}F_2N_3O_2S$ | 93-95° C. |
| 1-260* | | 2.56 |
| 1-261** | | 2.58 |
| 1-262 | | 4.24 |
| 1-263* | | 4.26 |
| 1-264** | | 4.26 |
| 1-265 | | 3.31 |
| 1-266* | | 3.30 |
| 1-267** | | 3.3 |
| 1-268 | | 3.71 |
| 1-269* | | 3.71 |
| 1-270** | | 3.71 |
| 1-271 | | 3.35 |
| 1-272* | | 3.35 |
| 1-273** | | 3.37 |
| 1-274 | | 4.3 |
| 1-275 | | 3.59 |
| 1-276 | | 3.91 |
| 1-277 | | 4.06 |
| 1-278 | | 1.84 |
| 1-279 | | 4.02 |
| 1-280 | | 5.03 |
| 1-281** | | 1.48 |
| 1-282** | | 3.53 |
| 1-283** | | 4.05 |
| 1-284** | | 4.18 |
| 1-285* | | |
| 1-286* | | |
| 1-287 | | 3.56 |
| 1-288 | | 4.85 |
| 1-289 | | 3.59 |
| 1-290 | | 5.0 |
| 1-291 | | 5.02 |
| 1-292 | | 5.02 |
| 1-293 | | 4.17 |
| 1-294 | | 4.57 |
| 1-295 | | 3.85 |
| 1-296 | | 4.05 |
| 1-297 | | 4.57 |
| 1-298 | | 4.68 |
| 1-299 | | 3.37 |
| 1-300 | | 3.33 |
| 1-301 | | 4.11 |
| 1-302 | | 3.75 |
| 1-303 | | 4.4 |
| 1-304 | | 4.17 |
| 1-305 | | 4.11 |
| 1-306 | | 3.7 |
| 1-307 | | 1.42 |
| 1-308* | | 3.62 |
| 1-309* | | 4.98 |
| 1-310* | | 4.92 |
| 1-311* | | 4.92 |
| 1-312* | | 4.15 |
| 1-313* | | 3.33 |
| 1-314* | | 3.78 |
| 1-315* | | 3.99 |
| 1-316* | | 4.51 |
| 1-317* | | 4.61 |
| 1-318* | | 4.56 |
| 1-319* | | 3.31 |
| 1-320* | | 4.1 |
| 1-321* | | 3.73 |
| 1-322* | | 4.35 |
| 1-323* | | 4.15 |
| 1-324* | | 4.1 |
| 1-325* | | 3.68 |
| 1-326* | | 4.04 |
| 1-327* | | 3.53 |
| 1-328* | | 4.77 |
| 1-329* | | 5.39 |
| 2-1 | $C_{15}H_{16}ClN_3S_2$ | 161-164° C. |
| 2-2 | $C_{14}H_{17}N_3OS$ | SOLID |
| 2-3 | $C_{16}H_{25}N_4OPS$ | OIL |
| 2-4 | $C_{16}H_{23}N_2O_3PS$ | OIL |
| 2-5 | $C_{12}H_{14}N_2S$ | 138-140° C. |
| 2-6 | $C_{12}H_{14}N_2S$ | 100-103° C. |
| 2-7 | $C_{12}H_{14}N_2S$ | 90-93° C. |
| 2-8 | $C_{12}H_{13}ClN_2S$ | 125-127° C. |
| 2-9 | $C_{18}H_{18}N_2S$ | 145-151° C. |
| 2-42 | | 3.75 |
| 2-43 | | 4.07 |
| 2-44 | | 3.80 |
| 2-45 | | |
| 2-46 | | 4.07 |
| 2-47 | | |
| 2-48 | | |
| 2-49 | | 4.31 |
| 2-50 | | 4.18 |
| 2-51* | | |
| 2-52** | | |
| 3-1 | $C_{11}H_{12}N_2O_2$ | 96-99° C. |
| 4-1 | $C_{11}H_{12}N_2OS$ | 136-137° C. |
| 5-1 | $C_{12}H_{14}N_2O_2$ | 159-162° C. |
| 5-2 | $C_{14}H_{18}N_2O_3$ | 141-142° C. |
| 6-1 | $C_{13}H_{16}N_2S$ | 160-162° C. |
| 6-34 | | 4.93 |
| 6-35 | | 4.32 |
| 6-36 | | 4.1 |
| 6-37 | | 4.49 |
| 6-38 | | |
| 6-39 | | |
| 6-40 | | |
| 6-41 | | |
| 6-42 | | |
| 6-43 | | |
| 6-44 | | |
| 6-45 | | |
| 7-1 | $C_{13}H_{16}N_2O$ | 112-113° C. |
| 7-34 | | 0.93 |
| 7-35** | | |
| 7-36 | | 2.57 |
| 7-37 | | 4.48 |
| 7-38 | | 3.51 |
| 7-39 | | 3.83 |
| 7-40 | | 1.67 |

TABLE 2-continued

Insecticidal Substituted Amino Heterocyclic and
Heteroaryl Derivatives Compound Characterization

| | Molecular Formula | Melting Point (° C.) of Solids Or Physical State or log P (HCOOH) [1] |
|---|---|---|
| 7-41 | | |
| 7-42 | | |
| 7-43 | | |
| 7-44 | | |
| 7-45 | | |
| 7-46* | | 2.56 |
| 7-47* | | 3.52 |
| 7-48* | | 4.52 |
| 7-49* | | 3.87 |
| 7-50* | | 3.84 |
| 7-51* | | 5.14 |
| 7-52* | | 5.08 |
| 7-53* | | 5.21 |
| 7-54* | | 4.3 |
| 7-55* | | 3.37 |
| 7-56* | | 3.94 |
| 7-57* | | 4.15 |
| 7-58* | | 4.67 |
| 7-59* | | 4.87 |
| 7-60* | | 4.72 |
| 7-61* | | 3.37 |
| 7-62* | | 4.3 |
| 7-63* | | 3.84 |
| 7-64* | | 4.61 |
| 7-65* | | 4.35 |
| 7-66* | | 4.35 |
| 7-67* | | 3.89 |
| 7-68* | | 4.2 |
| 7-69* | | 3.63 |
| 7-70* | | 4.92 |
| 7-71* | | 4.72 |
| 7-72 | | 3.84 |
| 7-73 | | 5.14 |
| 7-74 | | 5.14 |
| 7-75 | | 5.21 |
| 7-76 | | 4.3 |
| 7-77 | | 3.94 |
| 7-78 | | 4.72 |
| 7-79 | | 4.87 |
| 7-80 | | 4.77 |
| 7-81 | | 3.37 |
| 7-82 | | 4.3 |
| 7-83 | | 3.84 |
| 7-84 | | 4.67 |
| 7-85 | | 4.35 |
| 7-86 | | 4.35 |
| 7-87 | | 3.89 |
| 7-88 | | 4.2 |
| 7-89 | | 3.63 |
| 7-90 | | 4.92 |
| 7-91 | | 5.4 |
| 8-1 | | |
| 8-2 | | |
| 8-3 | | |
| 8-4 | | 1.08 |
| 8-5 | | 3.29 |
| 8-6 | | 3.81 |
| 8-7 | | 3.60 |
| 8-8 | | |
| 8-9 | | |
| 8-10 | | |
| 8-11 | | |
| 8-12 | | |
| 8-13 | | |
| 9-1 | | 1.64 |

The following table sets forth physical characterizing data for certain substituted ethyl carboxamide and thiocarboxamide intermediates of formula IA:

TABLE 2A

Substituted Ethyl Carboxamide and Thiocarboxamide
Intermediate Compound Characterization

| | Molecular Formula | Melting Point (° C.) of Solids Or Physical State or log P (HCOOH) [1] |
|---|---|---|
| IA-1 | $C_{12}H_{14}Cl_2N_2O$ | 170-171° C. |
| IA-2 | $C_{12}H_{15}ClN_2O$ | 149-150° C. |
| IA-3 | $C_{13}H_{17}ClN_2O$ | 160-162° C. |
| IA-4 | $C_{13}H_{17}ClN_2O$ | 179-180° C. |
| IA-5 | $C_{13}H_{17}ClN_2O$ | SOLID |
| IA-6 | $C_{12}H_{14}Cl_2N_2O$ | 169-170° C. |
| IA-7 | $C_{13}H_{17}ClN_2O_2$ | 148-149° C. |
| IA-8 | $C_{13}H_{17}ClN_2O_2$ | SOLID |
| IA-9 | $C_{12}H_{14}ClFN_2O$ | 150-151° C. |
| IA-10 | $C_{13}H_{17}ClN_2O$ | 105-116° C. |
| IA-11 | $C_{13}H_{17}ClN_2O$ | 168-172° C. |
| IA-12 | $C_{14}H_{19}ClN_2O$ | 163-168° C. |
| IA-13 | $C_{13}H_{16}ClFN_2O$ | 171-176° C. |
| IA-14 | $C_{12}H_{13}ClF_2N_2O$ | |
| IA-15 | $C_{12}H_{13}Cl_2FN_2O$ | LIQUID |
| IA-16 | $C_{12}H_{13}Cl_2FN_2O$ | |
| IA-17 | $C_{12}H_{15}ClN_2S$ | |
| IA-18 | $C_{13}H_{17}ClN_2S$ | |
| IA-19 | $C_{11}H_{13}ClN_2O_2$ | 171-172° C. |
| IA-20 | | 2.14 |
| IA-21 | | |
| I-A22* | | |
| IA-23* | | |
| IA-24 | | |
| IA-25* | | |

[1] log P (HCOOH) determined according to EEC-Directive 79/831, Annex V.A8 using HPLC (gradient method, acetonitrile/0.1% HCOOH)

Candidate insecticides were evaluated for insecticidal activity by observing mortality in a population of cotton aphid (*Aphis gossypii*) on treated cotton plants when compared to like populations of cotton aphid on untreated plants. These tests were conducted in the following manner:

For each rate of application of test compound, two seven- to-ten days old cotton seedlings (*Gossypium hirsutium*) grown in 7.6 cm diameter pots were selected for the test. Each test plant was infested with about 120 adult cotton aphids by placing onto each test plant cuttings of leaves from cotton plants grown in a cotton aphid colony. Once infested, the test plants were maintained for up to about 12 hours to allow complete translocation of the aphids onto the test plant. A solution comprising 1000 part per million (ppm) of each test compound was prepared by dissolving 10 milligrams of the test compound in 1 mL of acetone. Each solution was then diluted with 9 mL of a solution of 0.03 mL of polyoxyethylene (10) isooctylphenyl ether in 100 mL of water. About 2.5 mL of solution of each test compound was needed to spray each replicate of test plant (5 mL total for each test compound). If needed, the solution of 1000 ppm of test compound was serially diluted with a solution of 10% acetone and 300 ppm of polyoxyethylene (10) isooctylphenyl ether in water to provide solutions of each test compound for lower rates of application, for example, 300 ppm, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. For comparison purposes, a solution of 10% acetone and 300 ppm of polyoxyethylene (10) isooctylphenyl ether in water containing no test compound was also sprayed onto control test plants. Upon completion of spraying the solutions of test compound and the solution containing no test compound, the plants were allowed to dry. Upon completion of drying, the test and control plants were placed in a tray containing about 2.5 centimeters of water, where they were maintained in a growth chamber for 72 hours. After this time, each plant was assessed for percent mortality caused by the test compound when compared to the population of aphids that was infested onto the test plants prior to treatment with test compound. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was 40% mortality or less of the cotton aphid, the test compound was termed as inactive (I).

An assessment of the insecticidal activity at selected rates of application from this test is provided in Tables 3 and 3A. The test compounds of formula I are identified by numbers that correspond to those in Table 1.

ing 1000 part per million (ppm) of each test compound was prepared by dissolving 10 µl of the stock solution in 140 µl of an aqueous 0.003% Kinetic® (a nonionic wetter/spreader/penetrant adjuvant) solution. If needed, the solution of 1000 ppm of test compound was serially diluted with a solution of 66 mL of DMSO and 30 µl of Kinetic® in 934 mL of water (diluting solution) to provide solutions of each test compound for lower rates of application, for example, 300 ppm, 100 ppm, 30 ppm, or 10 ppm. Each replicate test plant disc was sprayed with 10 µl of the test solution at about 8 psi for 1 second. For comparison purposes, an aqueous solution of 0.003% Kinetic® containing no test compound and the dilut-

TABLE 3

The following compounds of the present invention reduced the population of cotton aphid (*Aphis gossypii*) between 40% and 100% when applied at an application rate of 1000 ppm or less:

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 1-1 | 1-2 | 1-3 | 1-4 | 1-5 | 1-6 | 1-7 | 1-8 | 1-9 | 1-10 |
| 1-11 | 1-12 | 1-13 | 1-14 | 1-15 | 1-16 | 1-17 | 1-18 | 1-19 | 1-20 |
| 1-21 | 1-22 | 1-23 | 1-24 | 1-25 | 1-26 | 1-27 | 1-28 | 1-29 | 1-30 |
| 1-31 | 1-32 | 1-33 | 1-34 | 1-35 | 1-36 | 1-230 | 1-231 | 1-232 | 1-234 |
| 1-235 | 1-238 | 1-240 | 1-241 | 1-242 | 1-243 | 1-244 | 1-245 | 1-246 | 1-247 |
| 1-248 | 1-249 | 1-257 | 2-1 | 2-3 | 2-4 | 2-5 | 2-6 | 2-7 | 2-8 |
| 2-10 | 3-1 | 4-1 | 5-1 | 5-2 | 6-1 | 7-1 | | | |

Candidate insecticides were also evaluated for cotton aphid insecticidal activity by observing mortality in a population of cotton aphid (*Aphis gossypii*) on treated cotton plant leaf discs when compared to like populations of cotton aphid on untreated plant leaf discs. These tests were conducted in the following manner:

Three week to one month-old cotton plants (*Gossypium hirsutium*) were prepared for infesting by cutting off the cotyledons and new true leaf growth, leaving the oldest two true leaves. To infest, two seven-to-ten day old cotton plants, grown in a cotton aphid colony were uprooted and lodged in the apex of the stem where the stems of the two true leaves meet with the main stem. Once infested, the test plants were maintained for up to about 12 hours to allow complete translocation of the aphids onto the leaves of the test plant. The wells of clear 128-well trays (CD-International, Pittman, N.J.) were filled with 1 mL of a warm, aqueous 3% agar solution and allowed to cool to ambient temperature. The aphid infested cotton leaves were removed from the plants and placed bottom side up on a cutting platform. Circular discs were cut from the infested leaves and placed bottom side up onto the cooled agar gel, one disc per well. Each leaf disc was visually inspected to assure that a minimum of 10 live aphids were present. A 50 mM stock solution of the test compound was prepared by dissolving the appropriate amount of the test compound in DMSO. A solution comprising solution containing no test compound were also sprayed onto test plant discs. Upon completion of spraying the solutions of test compound and the solutions containing no test compound, the plant discs were allowed to dry. Upon completion of drying, the test trays were covered with a plastic film. Three slits were made in the film over each well to allow air into each well. The test trays were placed in a biochamber (25° C., 16 hours light, 8 hours of dark and 35-40% relative humidity) for three days. After this time, each plant disc was assessed for percent mortality caused by the test compound when compared to the population of aphids that was infested onto the test plant discs containing no test compound. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was less than 40% mortality of the cotton aphid, the test compound was termed as inactive (I).

An assessment of the insecticidal activity at selected rates of application from this test is provided in Table 3A. The test compounds of formula I are identified by numbers that correspond to those in Table 1.

TABLE 3A

The following compounds of the present invention reduced the population of cotton aphid on treated leaf disks by 40% to 100% when applied at an application rate of 300 ppm or less:

| Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|
| 1-248 2-2 | 1-249 | 1-250 | 1-251 | 1-252 | 1-253 | 1-254 | 1-255 | 1-256 |

As set forth in Tables 3 and 3A the tested compounds of the present invention reduced the aphid population by at least 40% at an application rate of 1000 ppm or less.

Candidate insecticides were evaluated for insecticidal activity by observing mortality in a population of silverleaf whitefly (*Bemisia argentifolii*) on treated cotton plant cotyledons when compared to like populations of silverleaf whitefly on untreated plant cotyledons. These tests were conducted in the following manner:

For each rate of application of test compound, two four to six days old cotton seedlings (*Gossypium hirsutum*) grown in 3-inch diameter pots were selected for the test. Each test plant was sprayed with a test solution comprising 300 part per million (ppm), or less, of each test compound prepared by dissolving 12 milligrams of the test compound in 4 mL of acetone. Each solution was then diluted with 36 mL of a surfactant and water solution prepared by dissolving 0.03 gm of Triton X-100® surfactant in 100 mL of distilled water, providing a stock test solution of 300 ppm. About 2.5 mL of solution of each test compound was needed to spray each replicate of test plant (5 mL total for each test compound). If needed, the solution of 300 ppm of test compound was diluted with a solution of 10% acetone and 300 ppm of Triton X-100® surfactant in water to provide solutions of each test compound for lower rates of application, for example, 100 ppm, 30 ppm, or 10 ppm. Each replicate of test plant was sprayed with the solutions of test compound until run-off on both the upper and lower surfaces of the leaves. An the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. Upon completion of spraying the solutions of test compound and the solution containing no test compound, the plants were allowed to dry. Upon completion of drying, the test plants were excised at the soil surface and placed in a 1 ounce plastic cup containing a 2.5 cm filter paper moistened with 50 microliters of distilled water. Whiteflies (25-50) were added to each cup and a lid was placed on each. The test cups were maintained in a growth chamber for 72 hours at 70% relative humidity (light 12 hours/day). After this tune, each test was assessed for percent mortality caused by the test compound when compared to the population of whiteflies that were infested onto the test plants. A test compound was designated as possessing insecticidal activity (SA) if there was 40% to 75% mortality of silverleaf whitefly on plants sprayed with that compound. If there was 75% mortality or greater of the silverleaf whitefly, a test compound was designated as being more insecticidally active (A). If there was 40% mortality or less of the silverleaf whitefly, the test compound was termed as inactive (I).

An assessment of the insecticidal activity at selected rates of application from this test is provided in Table 4. The test compounds of formula I are identified by numbers that correspond to those in Table 1.

Candidate insecticides were evaluated for insecticidal activity by observing mortality in a population of tarnished plant bug nymphs (*Lygus lineolaris*) on treated broccoli plant leaves when compared to like populations of tarnished plant bug on untreated plant leaves. These tests were conducted in the following manner:

For each rate of application of test compound, four ten to fifteen days old broccoli seedlings (*Brassica oleracea*) grown in 3-inch diameter pots were selected for the test. Each test plant was sprayed with a test solution comprising 300 part per million (ppm), or less, of each test compound prepared by dissolving 12 milligrams of the test compound in 4 mL of acetone. Each solution was then diluted with 36 mL of a surfactant and water solution prepared by dissolving 0.03 gm of Triton X-100® surfactant in 100 mL of distilled water, providing a stock test solution of 300 ppm. About 2.5 mL of solution of each test compound was needed to spray each replicate of test plant (10 mL total for each test compound). If needed, the solution of 300 ppm of test compound was diluted with a solution of 10% acetone and 300 ppm of Triton X-100® surfactant in water to provide solutions of each test compound for lower rates of application, for example, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. Upon completion of spraying the solutions of test compound and the solution containing no test compound, the plants were allowed to dry. Upon completion of drying, the treated foliage was removed and two leaves were placed into an 8 ounce unwaxed paper cup which contained a one inch piece of cut cotton wick, moistened by soaking for five seconds with distilled water. Four late second to early third instar tarnished plant bug nymphs were placed into each cup and a lid was placed on each. The test cups were maintained in a growth chamber for 72 hours at 70% relative humidity (light 12 hours/day). After this time, each test was assessed for percent mortality caused by the test compound when compared to the population of tarnished plant bug nymphs that were infested onto the test plant leaves. A test compound was designated as possessing insecticidal activity (SA) if there was 40% to 75% mortality of tarnished leaf bug nymphs on plants sprayed with that compound. If there was 75% mortality or greater of the tarnished leaf bug nymphs, a test compound was designated as being more insecticidally active (A). If there was 40% mortality or less of the tarnished leaf bug nymphs, the test compound was termed as inactive (I).

An assessment of the insecticidal activity at selected rates of application from this test is provided in Table 5. The test compounds of formula I are identified by numbers that correspond to those in Table 1.

TABLE 4

The following compounds of the present invention reduced the population of silverleaf whitefly (*Bemisia argentifolii*) between 40% and 100% when applied at an application rate of 300 ppm or less:

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 1-2 | 1-21 | 1-26 | 1-27 | 1-34 | 1-35 | 1-233 | 1-234 | 1-235 | 1-236 |
| 1-237 | 1-238 | 1-239 | 1-240 | 1-242 | 1-243 | 1-244 | 1-245 | 1-247 | |

TABLE 5

The following compounds of the present invention reduced the population of tarnished leaf bug nymphs (*Lygus lineolaris*) between 40% and 100% when applied at an application rate of 300 ppm or less:

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 1-2 | 1-3 | 1-4 | 1-17 | 1-21 | 1-23 | | | | |

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An insecticidal composition comprising a compound of formula 1:

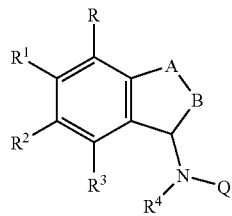

I wherein

A is —CHR$^5$—;

B is —CHR$^8$—;

R, R$^1$, R$^2$ and R$^3$ are hydrogen;

Q is:

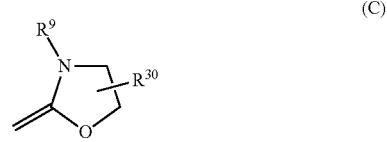

(C)

where
R$^4$ is taken together with the connecting atom in Q to form a double bond as in (C);
R$^9$ is —C(X)R$^{10}$, —C(X)OR$^{11}$, —C(X)SR$^{11}$, —C(X)NR$^{12}$R$^{13}$, —P(X)(OR$^{14}$)(OR$^{15}$) or P(X)(NR$^{16}$R$^{17}$)(NR$^{18}$R$^{19}$);
where R$^{10}$ is alkyl; R$^{11}$ is alkyl; R$^{12}$ and R$^{13}$ are independently selected from hydrogen, alkyl, alkoxyalkyl and alkoxycarbonylalkyl; R$^{14}$ and R$^{15}$ are independently selected from hydrogen and alkyl;
X is oxygen or sulfur;
R$^{16}$, R$^{17}$, R$^{18}$ and R$^{19}$ are independently selected from hydrogen and alkyl;
R$^5$ is hydrogen;
R$^8$ is hydrogen;
R$^{30}$ is hydrogen; and
agriculturally acceptable salts thereof.

2. An insecticidal composition as claimed in claim 1, further comprising one or more additional compounds selected from the group consisting of pesticides, plant growth regulators, fertilizers and soil conditioners.

* * * * *